(12) United States Patent
Guimarães et al.

(10) Patent No.: US 6,586,217 B1
(45) Date of Patent: Jul. 1, 2003

(54) MAMMALIAN SELENOPHOSPHATE SYNTHETASE

(75) Inventors: M. Jorge Guimarães, Mountain View; J. Fernando Bazan, Menlo Park; Albert Zlotnik, Palo Alto, all of CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/215,418

(22) Filed: Dec. 18, 1998

Related U.S. Application Data

(63) Continuation of application No. 08/406,359, filed on Mar. 17, 1995, now abandoned.

(51) Int. Cl.[7] ......................... C12N 15/12; C12N 15/54; C12N 9/12
(52) U.S. Cl. ....................... 435/194; 435/69.1; 435/325; 435/183; 435/6; 435/252.3; 435/91.2; 536/23.1; 536/23.2; 536/24.3; 536/24.31; 536/24.33; 514/44
(58) Field of Search ............................. 435/194.6, 252.3, 435/325, 183, 91.2; 536/23.2, 24.3, 24.31, 24.33; 514/44

(56) References Cited

PUBLICATIONS

[Ref A] Hillier et al. Unpublished, established Feb. 8, 1995, EST accession #T55907.*
[Ref B] Matoba et al., from Gene 146(2): 199–207, DDBJ Seq. Accession #D16990, Dec. 1, 1994.*
[Ref C] Adams et al., from Nature Genetics, 4: 373–380, EST accession #T09327, Aug. 3, 1993.*
[Ref D] Zlotnik et al. FASEB Journal 9(4): A833, Mar. 10, 1995.*

* cited by examiner

Primary Examiner—Rebecca E. Prouty
Assistant Examiner—Richard Hutson
(74) Attorney, Agent, or Firm—Edwin P. Ching

(57) ABSTRACT

Selenophosphate synthetase protein from a mammal, reagents related thereto including purified proteins, specific antibodies, and nucleic acids encoding this protein. Methods of using these reagents and diagnostic kits are also provided.

22 Claims, 3 Drawing Sheets

```
HuSPS   MAEA SATGACGEAMAAAEG SSGPAG- - -LTLGRSFSN YRPFE PQALGL SP SWRLTGFSGMK GCGCKVPQE    67
MoSPS   MAEA AAAGASGETMAALVA AEGSLGpagWSAGRSFSN YRPFE PQTLGF SP SWRLTSFSGMK GCGCKVPQE     70
EcSPS                                        MS EN SIRLTQYSHGA GCGCKISPK                24

HuSPS   ALLKL LAGLTRP DVRPPL GRGLVGG QEEA SQEAGLPAga gpspt fpalgigmds cviplrhgGLSLVQ TT  137
MoSPS   TLLKL LEGLTRP ALQPPITSGLVGG QEET VQEGGLSTrp gpgsa fpslsigmds cviplrhgGLSLVQ TT   140
EcSPS   VLETI LHSEQAK FVDPNLLVGNETR DDAA VYDLGN- - - - - - - - - - - - - - -GTSVIS TT    67

HuSPS   DFFYPLVED PYMMGRIACA NVL SDLYAMGitec dnmlmll svs qsmseeerek vtplMVKGFRDAAEEG G    207
MoSPS   DFFYPLVED PYMMGRIACA NVL SDLYAMGitec dnmlmll svs qsmsekerek vtplMIKGFRDAAEEG G    210
EcSPS   DFFMPIVDN PFDFGRIAAT NAI SDIFAMGgkpi maiailgwpi nklspeiare - - - -VTEGGRYACRQA G  133

HuSPS   TAVT GGQTV VN PWIIIGGVA TV VCQ PNEF IMPDS AVVGDV LVLTKPLGTQVA VNAHQ -WLDNPERwnkvk  276
MoSPS   TAVT GGQTV VN PWIIIGGVA TV VCQ QNEF IMPDS AVVGDV LVLTKPLGTQVA ANAHQ -WLDNPEKwnkik  279
EcSPS   IALA GGHSI DA PEPIFGLAV TG IVP TERV KKNST AQAGCK LFLTKPLGIGVL TTAEKkSLLKPEHqqlat   203

HuSPS m vvsreevela yqeamfnM A TLNRTAAGLMHTFNAHAATDITGFGILGHSQNLAKq - - - QRNEVSFVIHN      343
MoSPS m vvsreevela yqeamfnM A TLNRTAAGLMHTFNAHAATDITGFGILGHSQNLAKq - - - QKNEVSFVIHN      346
EcSPS e v- - - - - - -        MC RMNIAGASFANIEGVKAMTDVTGFGLLGHLSEMCQgagvQARVDYEAIPK      257

HuSPS   LPii - - - - - - -        AKMAAVskas - - - - - - GRFGLLQGTSAETSGGLL ICLp reqaa r- - - - - -  FCSE  389
MoSPS   LPii - - - - - - -        AKMAAIskas - - - - - - GRFGLLQGTSAETSGGLL ICLp reqaa r- - - - - -  FCSE  392
EcSPS   LPgveeyiklgavpggtte RNFASYghlmgempr EVRDLLCDP - - QTSGGLL LAVm peaen evkata AEFG   325

HuSPS   IKSSKY GEGHGawivgi vekgNRTARIIDK PRVIEVL PRG- ATAAVLAPDSSNASSE PSS                 448
MoSPS   IKSSKY GEGHGawivgi vekgNRTARIIDK PRVIEVL PRGASAAAAAAPDNSNAASE PSS                  452
EcSPS   IELTAI GELVDarggra mveir                                                          347
```

FIG. 2

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2202 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 138..1496

(ix) FEATURE:
      (A) NAME/KEY: misc_difference
      (B) LOCATION: replace(324..326, "tga")
      (D) OTHER INFORMATION: /note= "not a termination codon; actual
         natural protein contains a selenocysteine"

(xi) SEQUENCE DESCRIPTION: SEQ ID NO:1:

```
CGGACGTGGG CGAGTCCTCC GGTCCGGCTC GCGTGGTTGA TCATCTCCTG GCGTAACCTT        60

GGCCCGCTGT GGCTGGGAGA CTCATCTGCA GGTATCTGGG CCTTCTGGTC CGCACGGCCT       120

CCCGGGCGAG CGGCGCG ATG GCG GAA GCG GCG GCG GCG GGC GCC AGC GGA         170
                Met Ala Glu Ala Ala Ala Ala Gly Ala Ser Gly
                 1               5                  10

GAA ACC ATG GCG GCG CTA GTG GCC GCA GAA GGT TCC TTG GGC CCG GCG         218
Glu Thr Met Ala Ala Leu Val Ala Ala Glu Gly Ser Leu Gly Pro Ala
```

-continued

| | |
|---|---|
| GGC TGG TCT GCC GGC CGG AGT TTC TCC AAC TAC CGG CCG TTC GAG CCC<br>Gly Trp Ser Ala Gly Arg Ser Phe Ser Asn Tyr Arg Pro Phe Glu Pro<br>30                   35               40 | 266 |
| CAG ACA CTG GGC TTC AGC CCG AGC TGG CGG CTG ACG AGC TTC TCC GGC<br>Gln Thr Leu Gly Phe Ser Pro Ser Trp Arg Leu Thr Ser Phe Ser Gly<br>45               50              55 | 314 |
| ATG AAG GGC TGC GGC TGC AAG GTC CCC CAG GAG ACC CTG CTC AAA CTC<br>Met Lys Gly Cys Gly Cys Lys Val Pro Gln Glu Thr Leu Leu Lys Leu<br>60               65              70              75 | 362 |
| CTG GAG GGA CTG ACG CGG CCC GCG CTG CAG CCC CCG CTT ACC TCG GGT<br>Leu Glu Gly Leu Thr Arg Pro Ala Leu Gln Pro Pro Leu Thr Ser Gly<br>80               85              90 | 410 |
| CTG GTC GGG GGC CAG GAA GAG ACG GTG CAG GAA GGG GGC CTG TCC ACC<br>Leu Val Gly Gly Gln Glu Glu Thr Val Gln Glu Gly Gly Leu Ser Thr<br>95              100             105 | 458 |
| AGG CCC GGC CCC GGC TCA GCC TTC CCC TCG CTG AGC ATT GGC ATG GAC<br>Arg Pro Gly Pro Gly Ser Ala Phe Pro Ser Leu Ser Ile Gly Met Asp<br>110            115            120 | 506 |
| TCC TGC GTC ATC CCC CTG AGG CAC GGA GGC CTG TCG CTG GTG CAG ACC<br>Ser Cys Val Ile Pro Leu Arg His Gly Gly Leu Ser Leu Val Gln Thr<br>125            130            135 | 554 |
| ACC GAC TTC TTT TAC CCC TTG GTG GAA GAT CCC TAT ATG ATG GGG CGC<br>Thr Asp Phe Phe Tyr Pro Leu Val Glu Asp Pro Tyr Met Met Gly Arg<br>140            145            150           155 | 602 |
| ATA GCT TGT GCC AAT GTG CTC AGT GAC CTC TAT GCC ATG GGT ATC ACT<br>Ile Ala Cys Ala Asn Val Leu Ser Asp Leu Tyr Ala Met Gly Ile Thr<br>160            165            170 | 650 |
| GAG TGT GAC AAC ATG TTG ATG TTA CTC AGT GTG AGC CAG AGC ATG AGT<br>Glu Cys Asp Asn Met Leu Met Leu Leu Ser Val Ser Gln Ser Met Ser<br>175            180            185 | 698 |
| GAA AAG GAA CGA GAG AAG GTG ACA CCG CTC ATG ATC AAA GGC TTT CGT<br>Glu Lys Glu Arg Glu Lys Val Thr Pro Leu Met Ile Lys Gly Phe Arg<br>190            195            200 | 746 |
| GAC GCT GCG GAG GAG GGA GGC ACT GCA GTG ACC GGT GGA CAG ACA GTG<br>Asp Ala Ala Glu Glu Gly Gly Thr Ala Val Thr Gly Gly Gln Thr Val<br>205            210            215 | 794 |
| GTC AAC CCG TGG ATT ATC ATC GGT GGC GTT GCC ACG GTG GTG TGT CAG<br>Val Asn Pro Trp Ile Ile Ile Gly Gly Val Ala Thr Val Val Cys Gln<br>220            225            230           235 | 842 |
| CAA AAT GAA TTC ATA ATG CCT GAT AGT GCC GTG GTA GGA GAT GTG CTG<br>Gln Asn Glu Phe Ile Met Pro Asp Ser Ala Val Val Gly Asp Val Leu<br>240            245            250 | 890 |
| GTA TTA ACC AAA CCT TTA GGA ACC CAG GTT GCT GCC AAT GCC CAC CAA<br>Val Leu Thr Lys Pro Leu Gly Thr Gln Val Ala Ala Asn Ala His Gln<br>255            260            265 | 938 |
| TGG CTG GAT AAT CCT GAG AAA TGG AAT AAA ATC AAG ATG GTG GTT TCC<br>Trp Leu Asp Asn Pro Glu Lys Trp Asn Lys Ile Lys Met Val Val Ser<br>270            275            280 | 986 |
| AGA GAG GAA GTA GAG TTA GCC TAT CAG GAA GCT ATG TTC AAT ATG GCT<br>Arg Glu Glu Val Glu Leu Ala Tyr Gln Glu Ala Met Phe Asn Met Ala<br>285            290            295 | 1034 |
| ACT CTA AAC AGG ACT GCT GCT GGC TTG ATG CAC ACT TTT AAT GCC CAC<br>Thr Leu Asn Arg Thr Ala Ala Gly Leu Met His Thr Phe Asn Ala His<br>300            305            310           315 | 1082 |
| GCA GCC ACG GAT ATC ACA GGC TTT GGC ATA TTA GGA CAC TCT CAG AAC<br>Ala Ala Thr Asp Ile Thr Gly Phe Gly Ile Leu Gly His Ser Gln Asn<br>320            325            330 | 1130 |
| CTG GCA AAA CAG CAA AAA AAT GAA GTG TCC TTT GTC ATA CAT AAT CTG | 1178 |

```
Leu Ala Lys Gln Gln Lys Asn Glu Val Ser Phe Val Ile His Asn Leu
            335                 340                 345

CCA ATA ATT GCC AAG ATG GCT GCG ATC AGC AAA GCC AGT GGG CGC TTT      1226
Pro Ile Ile Ala Lys Met Ala Ala Ile Ser Lys Ala Ser Gly Arg Phe
        350                 355                 360

GGC CTC CTC CAA GGA ACG TCA GCT GAA ACC TCT GGG GGA TTA CTG ATT      1274
Gly Leu Leu Gln Gly Thr Ser Ala Glu Thr Ser Gly Gly Leu Leu Ile
365                 370                 375

TGT CTG CCA AGA GAG CAG GCG GCC CGC TTT TGT TCG GAA ATC AAA TCT      1322
Cys Leu Pro Arg Glu Gln Ala Ala Arg Phe Cys Ser Glu Ile Lys Ser
380                 385                 390                 395

TCC AAG TAC GGA GAG GGT CAC CAA GCT TGG ATC GTT GGC ATC GTG GAG      1370
Ser Lys Tyr Gly Glu Gly His Gln Ala Trp Ile Val Gly Ile Val Glu
                400                 405                 410

AAG GGA AAC CGG ACA GCC CGG ATC ATT GAC AAG CCT CGC GTT ATT GAA      1418
Lys Gly Asn Arg Thr Ala Arg Ile Ile Asp Lys Pro Arg Val Ile Glu
            415                 420                 425

GTT CTA CCT CGG GGA GCC TCT GCT GCT GCT GCT GCT CCT GAT AAT          1466
Val Leu Pro Arg Gly Ala Ser Ala Ala Ala Ala Ala Pro Asp Asn
        430                 435                 440

TCC AAC GCA GCC TCT GAG CCT AGT TCT TGA AATGGAATAG CGGTTGTTGG        1516
Ser Asn Ala Ala Ser Glu Pro Ser Ser  *
    445                 450

GAACTCGGAG CCATTCTACC CGCTCAGGGA CTGCTGGCCA GGGTTGATTT TAAGACCTTT    1576

CCAAAGGCTG CTTGCATGGT TCCTCCAGGC CCATCCAAAG CTTCCTGTAT GTGCATCCAG    1636

GCCTGTGAGT AATGGCGCTG CGGATGTGTG TTCATCTGTT GAGAGCATGA GGAGCAAAAA    1696

CCCGTTTCCC AAAGCAAGAG GAGGCTATTT CAGTTTTAGG GATTTTTTTT TTTTTTTTT     1756

TTTGCACTGA GTTGATTCAT TTCTGCACAG GGAGTAAAGA TTATTAAGAT TACATATGAG    1816

AAAAGTAAAC CTGCAACATG AAAAATTATT TGGACCAATA TATTGATAAA TCTAAATTGT    1876

TAGGAGAACT CTTACTGATT TATTGTCAAA TTTGTTATTA ATTTTTTTCT GAGAAACTGC    1936

CTCTTTTCCT GTTCTGGACA AGAGTTGAGC AGCTTGTCCG ACAGGAAAGG AAGACTAGCC    1996

ACCTGACTTG GTCTCTGATA ATGATGTCTC TCCCTCTAAC TCCCAGTAAG GACTGGGAGA    2056

GGCTGAACAA ACCTCAGAGC CAGGTGTCGG TGGCCATTGA ATCTTACACT GAAACTTCTG    2116

GAGATTTAAT TAATAAAGAG AATTTCTTAC AGTAACTAAA TAAAAGGGCT TTGTTGGAAA    2176

AAAAAAAAAA AAAAAAAAA AAAAA                                           2202

(2) INFORMATION FOR SEQ ID NO:2:

(i) SEQUENCE CHARACTERISTICS:
        (A) LENGTH: 452 amino acids
        (B) TYPE: amino acid
        (D) TOPOLOGY: linear (ii) MOLECULE TYPE: protein (xi) SEQUENCE DESCRIPTION: SEQ ID NO:2:

Met Ala Glu Ala Ala Ala Gly Ala Ser Gly Glu Thr Met Ala Ala
1               5                   10                  15

Leu Val Ala Ala Glu Gly Ser Leu Gly Pro Ala Gly Trp Ser Ala Gly
            20                  25                  30

Arg Ser Phe Ser Asn Tyr Arg Pro Phe Glu Pro Gln Thr Leu Gly Phe
        35                  40                  45

Ser Pro Ser Trp Arg Leu Thr Ser Phe Ser Gly Met Lys Gly Cys Gly
    50                  55                  60
```

-continued

```
Cys Lys Val Pro Gln Glu Thr Leu Leu Lys Leu Leu Glu Gly Leu Thr
 65                  70                  75                  80

Arg Pro Ala Leu Gln Pro Pro Leu Thr Ser Gly Leu Val Gly Gly Gln
                 85                  90                  95

Glu Glu Thr Val Gln Glu Gly Gly Leu Ser Thr Arg Pro Gly Pro Gly
            100                 105                 110

Ser Ala Phe Pro Ser Leu Ser Ile Gly Met Asp Ser Cys Val Ile Pro
        115                 120                 125

Leu Arg His Gly Gly Leu Ser Leu Val Gln Thr Thr Asp Phe Phe Tyr
    130                 135                 140

Pro Leu Val Glu Asp Pro Tyr Met Met Gly Arg Ile Ala Cys Ala Asn
145                 150                 155                 160

Val Leu Ser Asp Leu Tyr Ala Met Gly Ile Thr Glu Cys Asp Asn Met
                165                 170                 175

Leu Met Leu Leu Ser Val Ser Gln Ser Met Ser Glu Lys Glu Arg Glu
            180                 185                 190

Lys Val Thr Pro Leu Met Ile Lys Gly Phe Arg Asp Ala Ala Glu Glu
        195                 200                 205

Gly Gly Thr Ala Val Thr Gly Gly Gln Thr Val Val Asn Pro Trp Ile
    210                 215                 220

Ile Ile Gly Gly Val Ala Thr Val Val Cys Gln Gln Asn Glu Phe Ile
225                 230                 235                 240

Met Pro Asp Ser Ala Val Val Gly Asp Val Leu Val Leu Thr Lys Pro
                245                 250                 255

Leu Gly Thr Gln Val Ala Ala Asn Ala His Gln Trp Leu Asp Asn Pro
            260                 265                 270

Glu Lys Trp Asn Lys Ile Lys Met Val Val Ser Arg Glu Glu Val Glu
        275                 280                 285

Leu Ala Tyr Gln Glu Ala Met Phe Asn Met Ala Thr Leu Asn Arg Thr
    290                 295                 300

Ala Ala Gly Leu Met His Thr Phe Asn Ala His Ala Ala Thr Asp Ile
305                 310                 315                 320

Thr Gly Phe Gly Ile Leu Gly His Ser Gln Asn Leu Ala Lys Gln Gln
                325                 330                 335

Lys Asn Glu Val Ser Phe Val Ile His Asn Leu Pro Ile Ile Ala Lys
            340                 345                 350

Met Ala Ala Ile Ser Lys Ala Ser Gly Arg Phe Gly Leu Leu Gln Gly
        355                 360                 365

Thr Ser Ala Glu Thr Ser Gly Gly Leu Leu Ile Cys Leu Pro Arg Glu
    370                 375                 380

Gln Ala Ala Arg Phe Cys Ser Glu Ile Lys Ser Ser Lys Tyr Gly Glu
385                 390                 395                 400

Gly His Gln Ala Trp Ile Val Gly Ile Val Glu Lys Gly Asn Arg Thr
                405                 410                 415

Ala Arg Ile Ile Asp Lys Pro Arg Val Ile Glu Val Leu Pro Arg Gly
            420                 425                 430

Ala Ser Ala Ala Ala Ala Ala Pro Asp Asn Ser Asn Ala Ala Ser
        435                 440                 445

Glu Pro Ser Ser
    450
```

(2) INFORMATION FOR SEQ ID NO:3:

(i) SEQUENCE CHARACTERISTICS:

```
    (A) LENGTH: 1932 base pairs
    (B) TYPE: nucleic acid
    (C) STRANDEDNESS: single
    (D) TOPOLOGY: linear (ii) MOLECULE TYPE: cDNA (ix) FEATURE:
    (A) NAME/KEY: CDS
    (B) LOCATION: 139..1485

(ix) FEATURE:
    (A) NAME/KEY: misc_difference
    (B) LOCATION: replace(316..318, "tga")
    (D) OTHER INFORMATION: /note= "not a termination codon;
        natural protein contains a selenocysteine"

(ix) FEATURE:
    (A) NAME/KEY: unsure
    (B) LOCATION: replace(1787..1789, "gcc")

(ix) FEATURE:
    (A) NAME/KEY: unsure
    (B) LOCATION: replace(1787..1789, "gcg")

(ix) FEATURE:
    (A) NAME/KEY: unsure
    (B) LOCATION: replace(1787..1789, "gct")

(xi) SEQUENCE DESCRIPTION: SEQ ID NO:3:
```

```
GTGCATGCCG TGGGTCTGAC GGCTTGAGTA GCGCTAGGGA GAATCCCTGC AGGTAATATT      60

TGACTTTTGC TTCATATTAA TCTGAGTGGA AAATAAAAGG GCCCTCTTCT CCTCTCGCTT     120

CCCTGCCGGG CAGGCGCC ATG GCG GAA GCC TCG GCG ACG GGC GCC TGC GGA      171
                    Met Ala Glu Ala Ser Ala Thr Gly Ala Cys Gly
                     1               5                  10

GAG GCG ATG GCA GCG GCG GAA GGC TCC TCG GGC CCG GCG GGC TTG ACT      219
Glu Ala Met Ala Ala Ala Glu Gly Ser Ser Gly Pro Ala Gly Leu Thr
             15                  20                  25

CTG GGC CGG AGC TTC TCG AAC TAC CGG CCC TTC GAG CCC CAG GCG TTG      267
Leu Gly Arg Ser Phe Ser Asn Tyr Arg Pro Phe Glu Pro Gln Ala Leu
         30                  35                  40

GGC CTC AGC CCG AGC TGG CGG CTG ACG GGC TTC TCC GGC ATG AAG GGC      315
Gly Leu Ser Pro Ser Trp Arg Leu Thr Gly Phe Ser Gly Met Lys Gly
     45                  50                  55

TGC GGC TGC AAG GTC CCG CAG GAG GCG CTG CTC AAA CTC CTG GCG GGA      363
Cys Gly Cys Lys Val Pro Gln Glu Ala Leu Leu Lys Leu Leu Ala Gly
60                  65                  70                  75

CTG ACG CGG CCG GAC GTG CGG CCC CCG CTG GGC CGG GGC CTG GTG GGT      411
Leu Thr Arg Pro Asp Val Arg Pro Pro Leu Gly Arg Gly Leu Val Gly
                 80                  85                  90

GGC CAG GAA GAG GCG TCC CAG GAA GCC GGC CTG CCG GCA GGA GCG GGC      459
Gly Gln Glu Glu Ala Ser Gln Glu Ala Gly Leu Pro Ala Gly Ala Gly
             95                 100                 105

CCC AGC CCC ACC TTT CCA GCC CTG GGC ATC GGG ATG GAC TCC TGC GTC      507
Pro Ser Pro Thr Phe Pro Ala Leu Gly Ile Gly Met Asp Ser Cys Val
         110                 115                 120

ATC CCC CTG AGG CAC GGG GGC CTG TCA CTG GTG CAG ACC ACG GAC TTC      555
Ile Pro Leu Arg His Gly Gly Leu Ser Leu Val Gln Thr Thr Asp Phe
     125                 130                 135

TTT TAC CCC TTG GTA GAA GAT CCC TAC ATG ATG GGG CGC ATA GCT TGT      603
Phe Tyr Pro Leu Val Glu Asp Pro Tyr Met Met Gly Arg Ile Ala Cys
140                 145                 150                 155

GCC AAC GTG CTG AGT GAC CTC TAC GCC ATG GGG ATT ACT GAG TGT GAC      651
Ala Asn Val Leu Ser Asp Leu Tyr Ala Met Gly Ile Thr Glu Cys Asp
                 160                 165                 170
```

```
AAC ATG TTG ATG TTA CTC AGC GTC AGC CAG AGT ATG AGT GAG GAG GAA        699
Asn Met Leu Met Leu Leu Ser Val Ser Gln Ser Met Ser Glu Glu Glu
            175                 180                 185

CGC GAA AAG GTA ACG CCA CTC ATG GTC AAA GGC TTT CGG GAT GCG GCT        747
Arg Glu Lys Val Thr Pro Leu Met Val Lys Gly Phe Arg Asp Ala Ala
            190                 195                 200

GAG GAA GGA GGG ACG GCA GTG ACC GGT GGG CAA ACG GTG GTC AAC CCT        795
Glu Glu Gly Gly Thr Ala Val Thr Gly Gly Gln Thr Val Val Asn Pro
            205                 210                 215

TGG ATT ATA ATC GGT GGA GTT GCC ACT GTA GTA TGC CAA CCA AAT GAG        843
Trp Ile Ile Ile Gly Gly Val Ala Thr Val Val Cys Gln Pro Asn Glu
220                 225                 230                 235

TTC ATA ATG CCG GAC AGC GCC GTC GTT GGG GAC GTG CTG GTG TTA ACC        891
Phe Ile Met Pro Asp Ser Ala Val Val Gly Asp Val Leu Val Leu Thr
            240                 245                 250

AAA CCG TTA GGA ACC CAG GTT GCT GTC AAT GCC CAC CAA TGG CTG GAT        939
Lys Pro Leu Gly Thr Gln Val Ala Val Asn Ala His Gln Trp Leu Asp
            255                 260                 265

AAT CCT GAA AGA TGG AAT AAA GTA AAG ATG GTG GTC TCC AGA GAA GAG        987
Asn Pro Glu Arg Trp Asn Lys Val Lys Met Val Val Ser Arg Glu Glu
            270                 275                 280

GTG GAG CTG GCC TAT CAG GAA GCC ATG TTC AAT ATG GCT ACC CTC AAC       1035
Val Glu Leu Ala Tyr Gln Glu Ala Met Phe Asn Met Ala Thr Leu Asn
            285                 290                 295

AGA ACT GCT GCA GGT TTA ATG CAC ACA TTT AAT GCC CAT GCG GCC ACA       1083
Arg Thr Ala Ala Gly Leu Met His Thr Phe Asn Ala His Ala Ala Thr
300                 305                 310                 315

GAT ATC ACA GGC TTT GGC ATT CTA GGA CAC TCC CAG AAC CTT GCA AAA       1131
Asp Ile Thr Gly Phe Gly Ile Leu Gly His Ser Gln Asn Leu Ala Lys
            320                 325                 330

CAA CAA AGA AAT GAA GTG TCC TTT GTT ATT CAT AAT CTG CCA ATA ATT       1179
Gln Gln Arg Asn Glu Val Ser Phe Val Ile His Asn Leu Pro Ile Ile
            335                 340                 345

GCC AAG ATG GCT GCC GTC AGC AAG GCC AGT GGA CGG TTT GGG CTT CTT       1227
Ala Lys Met Ala Ala Val Ser Lys Ala Ser Gly Arg Phe Gly Leu Leu
            350                 355                 360

CAA GGA ACC TCA GCT GAA ACC TCT GGG GGA TTA CTG ATT TGT CTG CCA       1275
Gln Gly Thr Ser Ala Glu Thr Ser Gly Gly Leu Leu Ile Cys Leu Pro
            365                 370                 375

AGA GAA CAG GCG GCT CGC TTT TGT TCT GAA ATC AAA TCC TCC AAG TAC       1323
Arg Glu Gln Ala Ala Arg Phe Cys Ser Glu Ile Lys Ser Ser Lys Tyr
380                 385                 390                 395

GGA GAG GGT CAC CAA GCG TGG ATC GTT GGC ATT GTG GAA AAG GGA AAC       1371
Gly Glu Gly His Gln Ala Trp Ile Val Gly Ile Val Glu Lys Gly Asn
            400                 405                 410

CGA ACG GCC CGG ATC ATT GAC AAG CCG CGA GTT ATT GAA GTC CTG CCT       1419
Arg Thr Ala Arg Ile Ile Asp Lys Pro Arg Val Ile Glu Val Leu Pro
            415                 420                 425

CGT GGG GCC ACA GCT GCT GTT CTT GCT CCT GAC AGT TCA AAT GCC TCC       1467
Arg Gly Ala Thr Ala Ala Val Leu Ala Pro Asp Ser Ser Asn Ala Ser
            430                 435                 440

TCT GAG CCT AGC TCG TGA GATGAAAGAA CAGAAGTTGT TTGGACCTTA              1515
Ser Glu Pro Ser Ser  *
            445

GAGCCATTGT CCACAATCAC GGATGGTTCT CAAGAGTTGA TTGTAAGAAA TTTCCAAAGA     1575

AGGCTGCCTG CATAGTGGTT CCGGCTGCCC TTTCTAGGTG ATTGGAATCA GCCCATCTAA     1635

AGCAGTCTTT ATATGCATTC CGAGGCCAGA GTAACATTTT GAACTTTGGG GGGATATTTG     1695

TTCATCACTT GGGTAGAAGA GGAGCAAAAA TACTTCTGTT TTCTCTTGCC AAAGTAAGAT     1755
```

-continued

```
GAAGCTATTC CAGGTTGAGG GATTTTTCTT TGCACGGGGT TGATTAATTT CTGCACAGGG    1815

AGTGAGATTA TTAAAGTAAC ACACACACAA AGTAAATTGC AAAATGAAAA AAATTAGAAG    1875

CAAATGAGTT TTGGACCAAT ATTGTTGATA AATCTAAATT GTTAAGAGAG ATCTTAT      1932
```

(2) INFORMATION FOR SEQ ID NO:4:

(i) SEQUENCE CHARACTERISTICS:
        (A) LENGTH: 448 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Glu Ala Ser Ala Thr Gly Ala Cys Gly Glu Ala Met Ala Ala
  1               5                  10                  15

Ala Glu Gly Ser Ser Gly Pro Ala Gly Leu Thr Leu Gly Arg Ser Phe
                 20                  25                  30

Ser Asn Tyr Arg Pro Phe Glu Pro Gln Ala Leu Gly Leu Ser Pro Ser
             35                  40                  45

Trp Arg Leu Thr Gly Phe Ser Gly Met Lys Gly Cys Gly Cys Lys Val
         50                  55                  60

Pro Gln Glu Ala Leu Leu Lys Leu Leu Ala Gly Leu Thr Arg Pro Asp
 65                  70                  75                  80

Val Arg Pro Pro Leu Gly Arg Gly Leu Val Gly Gln Glu Glu Ala
                 85                  90                  95

Ser Gln Glu Ala Gly Leu Pro Ala Gly Ala Pro Ser Pro Thr Phe
                100                 105                 110

Pro Ala Leu Gly Ile Gly Met Asp Ser Cys Val Ile Pro Leu Arg His
                115                 120                 125

Gly Gly Leu Ser Leu Val Gln Thr Thr Asp Phe Phe Tyr Pro Leu Val
            130                 135                 140

Glu Asp Pro Tyr Met Met Gly Arg Ile Ala Cys Ala Asn Val Leu Ser
145                 150                 155                 160

Asp Leu Tyr Ala Met Gly Ile Thr Glu Cys Asp Asn Met Leu Met Leu
                165                 170                 175

Leu Ser Val Ser Gln Ser Met Ser Glu Glu Arg Glu Lys Val Thr
                180                 185                 190

Pro Leu Met Val Lys Gly Phe Arg Asp Ala Ala Glu Glu Gly Gly Thr
            195                 200                 205

Ala Val Thr Gly Gly Gln Thr Val Val Asn Pro Trp Ile Ile Ile Gly
        210                 215                 220

Gly Val Ala Thr Val Val Cys Gln Pro Asn Glu Phe Ile Met Pro Asp
225                 230                 235                 240

Ser Ala Val Val Gly Asp Val Leu Val Leu Thr Lys Pro Leu Gly Thr
                245                 250                 255

Gln Val Ala Val Asn Ala His Gln Trp Leu Asp Asn Pro Glu Arg Trp
            260                 265                 270

Asn Lys Val Lys Met Val Val Ser Arg Glu Glu Val Glu Leu Ala Tyr
        275                 280                 285

Gln Glu Ala Met Phe Asn Met Ala Thr Leu Asn Arg Thr Ala Ala Gly
    290                 295                 300

Leu Met His Thr Phe Asn Ala His Ala Ala Thr Asp Ile Thr Gly Phe
305                 310                 315                 320
```

```
Gly Ile Leu Gly His Ser Gln Asn Leu Ala Lys Gln Gln Arg Asn Glu
            325                 330                 335

Val Ser Phe Val Ile His Asn Leu Pro Ile Ile Ala Lys Met Ala Ala
            340                 345                 350

Val Ser Lys Ala Ser Gly Arg Phe Gly Leu Leu Gln Gly Thr Ser Ala
            355                 360                 365

Glu Thr Ser Gly Gly Leu Leu Ile Cys Leu Pro Arg Glu Gln Ala Ala
            370                 375                 380

Arg Phe Cys Ser Glu Ile Lys Ser Ser Lys Tyr Gly Glu Gly His Gln
385                 390                 395                 400

Ala Trp Ile Val Gly Ile Val Glu Lys Gly Asn Arg Thr Ala Arg Ile
            405                 410                 415

Ile Asp Lys Pro Arg Val Ile Glu Val Leu Pro Arg Gly Ala Thr Ala
            420                 425                 430

Ala Val Leu Ala Pro Asp Ser Ser Asn Ala Ser Ser Glu Pro Ser Ser
            435                 440                 445
```

(2) INFORMATION FOR SEQ ID NO:5:

(i) SEQUENCE CHARACTERISTICS:
        (A) LENGTH: 347 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: E. coli (xi) SEQUENCE DESCRIPTION: SEQ ID NO:5:

```
Met Ser Glu Asn Ser Ile Arg Leu Thr Gln Tyr Ser His Gly Ala Gly
1               5                   10                  15

Cys Gly Cys Lys Ile Ser Pro Lys Val Leu Glu Thr Ile Leu His Ser
            20                  25                  30

Glu Gln Ala Lys Phe Val Asp Pro Asn Leu Leu Val Gly Asn Glu Thr
            35                  40                  45

Arg Asp Asp Ala Ala Val Tyr Asp Leu Gly Asn Gly Thr Ser Val Ile
50                  55                  60

Ser Thr Thr Asp Phe Phe Met Pro Ile Val Asp Asn Pro Phe Asp Phe
65                  70                  75                  80

Gly Arg Ile Ala Ala Thr Asn Ala Ile Ser Asp Ile Phe Ala Met Gly
            85                  90                  95

Gly Lys Pro Ile Met Ala Ile Ala Ile Leu Gly Trp Pro Ile Asn Lys
            100                 105                 110

Leu Ser Pro Glu Ile Ala Arg Glu Val Thr Glu Gly Gly Arg Tyr Ala
            115                 120                 125

Cys Arg Gln Ala Gly Ile Ala Leu Ala Gly Gly His Ser Ile Asp Ala
            130                 135                 140

Pro Glu Pro Ile Phe Gly Leu Ala Val Thr Gly Ile Val Pro Thr Glu
145                 150                 155                 160

Arg Val Lys Lys Asn Ser Thr Ala Gln Ala Gly Cys Lys Leu Phe Leu
            165                 170                 175

Thr Lys Pro Leu Gly Ile Gly Val Leu Thr Thr Ala Glu Lys Lys Ser
            180                 185                 190

Leu Leu Lys Pro Glu His Gly Gly Leu Ala Thr Glu Val Met Cys Arg
            195                 200                 205
```

-continued

```
Met Asn Ile Ala Gly Ala Ser Phe Ala Asn Ile Glu Gly Val Lys Ala
    210                 215                 220

Met Thr Asp Val Thr Gly Phe Gly Leu Leu Gly His Leu Ser Glu Met
225                 230                 235                 240

Cys Gln Gly Ala Gly Val Gln Ala Arg Val Asp Tyr Glu Ala Ile Pro
                245                 250                 255

Lys Leu Pro Gly Val Glu Glu Tyr Ile Lys Leu Gly Ala Val Pro Gly
            260                 265                 270

Gly Thr Glu Arg Asn Phe Ala Ser Tyr Gly His Leu Met Gly Glu Met
        275                 280                 285

Pro Arg Glu Val Arg Asp Leu Leu Cys Asp Pro Gln Thr Ser Gly Gly
    290                 295                 300

Leu Leu Leu Ala Val Met Pro Glu Ala Glu Asn Glu Val Lys Ala Thr
305                 310                 315                 320

Ala Ala Glu Phe Gly Ile Glu Leu Thr Ala Ile Gly Glu Leu Val Pro
                325                 330                 335

Ala Arg Gly Gly Arg Ala Met Val Glu Ile Arg
            340                 345
```

MAMMALIAN SELENOPHOSPHATE SYNTHETASE

This application is a continuation of commonly assigned, application No. 08/406,359, filed Mar. 17, 1995 now abandoned, which is incorporated herein by reference.

FIELD OF THE INVENTION

The present invention pertains to compositions related to proteins which function in controlling development and differentiation of mammalian cells, e.g., cells of a mammalian immune system. In particular, it provides proteins which exhibit an enzymatic activity of phosphorylating a selenium compound to produce a selenophosphate, a first step in the production of a selenocysteine, which is incorporated into various proteins.

BACKGROUND OF THE INVENTION

Selenocysteine was identified as the selenium moiety in a number of prokaryotic and eukaryotic proteins. See, e.g., Stadtman, (1991) *J. Biol. Chem.* 266:1625–16260; and Berry, et al (1993) *Biochem Soc. Trans.* 21:827–832. The presence of selenocysteine in proteins was shown to be responsible for a substantial increase in their enzymatic activity relatively to their cysteine-containing counterparts. See, e.g., Axley et al. (1990) *J. Biol. Chem.* 265:18213–18218; Axley, et al. (1991) *J Biol. Chem.* 266:13731–13736; Axley, et al. (1991) *Proc. Nat'l Acad. Sci. USA* 88:8450–8454; and Berry, et al. (1991) *Nature* 349:438–440. Selenocysteine is located in the active site of three different groups of bacterial enzymes: glycine reductase, see, e.g., Garcia, et al. (1992) *J. Bacteriol.* 174:7080–9, formate dehydrogenases, see, e.g., Zinoni, et al. (1987) *Proc. Natl. Acad. Sci. USA* 84:3156–3160; and Berg, et al. (1991) *J. Biol. Chem.* 266:22380–22385, and hydrogenases, see, e.g., Stadtman (1990) *Ann. Rev. Biochem.* 59:111–127. A number of selenocysteine containing proteins have also been described in mammalian organisms. These include the Cytoplasmic, see, e.g., Flohé, et al. (1979) *FEBS Letts* 32:132–134; Plasma, see, e.g., Takahashi, et al. (1987) *Arch. Biochem. Biophys* 256:677–686; and Maddipati, et al. (1987). *J. Biol. Chem* 262:17396–17403; Phospholipid Hydroperoxide Glutathione Peroxidases, see, e.g., Ursini, et al. (1985) *Biochim. Biophys. Acta* 839:62–70; and Schuckelt, et al. (1991) *Free Radical Res. Commun.* 14:343–361; Type I iodothyronine deiodinase, see, e.g., Behne, et al. (1990) *Biochem. Byophis. Res. Commun.* 173:1143–1149; and Berry, et al. (1991) *Nature* 349:438–440; Selenoprotein P. see, e.g., Read, et al. (1990) *J. Biol. Chem* 265:17899–17905; and Hill, et al. (1991) *J. Biol. Chem.* 265:10060–10063; and Selenoprotein of the Sperm Mitochondrial Capsule, see, e.g., Kleene, et al. (1990) *Dev. Biol.* 137:395–402; and Karimpour, et al. (1992) *DNA and Cell Biology* 11:693–699. With notable exceptions, these proteins catalyze oxidation-reduction reactions and some act as peroxide scavengers, see, e.g., Stadtman (1990). *Ann. Rev. Biochem.* 59:111–127.

As in bacteria, see, e.g., Zinoni, et al. (1990) *Proc. Natl Acad. Sci. USA* 87:4660–4664; and Heider, et al. (1992) *EMBO J.* 11:3759–3766, the incorporation of selenocysteine in eukaryotic proteins is directed by UGA codons, commonly read as stop codons by the translational machinery. See, e.g., Bock, et al. (1991) *TIBS* 16:463–467; and Berry and Larsen (1993) *Biochem. Soc. Trans.* 21:827–832. The co-translational insertion of selenocysteine in the polypeptide chain is made possible by the existence of a specific secondary structure in selenoprotein-encoding mRNAs, see, e.g., Zinoni, et al. (1990) *Proc. Natl Acad. Sci. USA* 87:4660–4664; Heider, et al. (1992) *EMBO J.* 11:3759–3766; and Berry, et al (1993) *EMBO J.* 12:3315–3322. Stem-loops have been described in bacterial selenocysteine-encoding mRNAs, which are located inside the translating region, immediately after the UGA codon, and are required for the incorporation of selenocysteine into bacterial proteins. See, e.g., Zinoni, et al. (1990) *Proc. Natl Acad. Sci. USA* 87:4660–4664; and Heider, et al. (1992) *EMBO J.* 11:3759–3766. On the other hand, stem-loops, structurally different from their bacterial homologues, have been identified in the 3' untranslated region of eukaryotic mRNAs encoding selenocysteine-containing proteins. These mRNA structures, designated SECIS elements, see, e.g., Berry, et al (1993). *EMBO J.* 12:3315–3322, are required for the UGA directed incorporation of selenocysteine into eukaryotic proteins. Specific tRNAs, designated tRNA(ser) sec, complementary to the UGA codons, were described both in bacteria, see, e.g., Leinfelder, et al. (1990) *Proc. Natl. Acad. Sci. USA* 87:543–547; and Heider, et al. (1989) *Nucleic Acids Res.* 17:2529–2540; and eukaryotic organisms, see, e.g., Lee, et al. (1990) *Mol. Cel. Biol.* 10:1940–1949; and Hatfield, et al. (1992) *Biochem. Biophys. Res. Commun.* 184:254–259. Furthermore, a specific elongation factor necessary for the incorporation of selenocysteine into proteins, designated SELB, was isolated in bacterial organisms, see, e.g., Forchhammer, et al. (1989) *Nature* 342:453–456. This elongation factor was shown to bind to the loop region of the hairpin structure required for selenocysteine incorporation. In the presence of selenocysteine-tRNA, SELB was shown to interact with selenocysteine-tRNA and GTP to form a ternary complex that recognizes the ribosome bound mRNA forming a selenocysteinyl-tRNA-SELB-GTP-mRNA complex that can tether protein factors to the translational complex during protein synthesis, see, e.g., Baron, et al. (1993) *Proc. Natl. Acad. Sci. USA* 90:4181–4185; and Ringquist, et al. (1994) *Genes and Development* 8:376–385.

Enzymatic reactions required for the synthesis of selenocysteine have been described in bacterial organisms. First, monoselenophosphate (MSP) is synthesized from selenide and ATP in an enzymatic reaction catalyzed by SPS. See, e.g., Veres, et al. (1994) *J. Biol. Chem.* 269:10597–10603. MSP is a highly reactive compound, see, e.g., Glass, et al. (1993) *Biochemistry* 32:12555–9; and Stadtman (1994) *Biofactors* 4:181–185, used as an active selenium donor in the synthesis of selenocysteine from seryl-tRNAs. See Leinfelder, et al. (1990) *Proc. Natl. Acad. Sci. USA* 87:543–547. Additionally, MSP is required for an entirely different process: the posttranscriptional modification of 2-thiouridine tRNAS in which sulfur is replaced with selenium forming 2-selenouridine tRNAs, see, e.g., Leinfelder, et al. (1990) *Proc. Natl. Acad. Sci. USA* 87:543–547; Veres, et al. (1992) *Proc. Natl. Acad. Sci. USA* 89:2975–2979; and Veres and Stadtman (1994) *Proc. Natl. Acad. Sci. USA* 91:8092–8096.

However, the isolation of a mammalian counterpart enzyme has eluded biochemists for years. As such, the elucidation of whether similar mechanisms of regulation and expression occur in mammals has not been determined. Moreover, in the absence of ready sources of selenophosphate and selenocysteine-tRNAS, further discovery of what other proteins useful in various developmental and regulatory pathways has remained a mystery. The present invention solves these and many other needs.

SUMMARY OF THE INVENTION

The present invention is based, in part, upon the discovery of mammalian selenocysteine-containing enzymes. It embraces means to use the enzymes to screen for chemical modulators of the selenophosphate synthetase (SPS), e.g., mutations (muteins) of the natural sequences, fusion proteins, and other structural or functional analogs. Isolation of the proteins allows also for production of antibodies at high efficiency. The invention also embraces isolated genes and fragments thereof encoding proteins of the invention. Various uses of these different protein or nucleic acid compositions are also provided.

The present invention provides:
1. A sustantially pure or isolated protein comprising a fragment exhibiting sequence homology to a corresponding portion of a mammalian selonophosphate synthetase wherein:
   a) said homology is at least about 90% identity and said portion is at least about 9 amino acids;
   b) said homology is at least about 80% identity and said portion is at least about 17 amino acids; or
   a) said homology is at least about 700% identity and said portion is at least about 25 amino acids;
2. The protein of claim 1, wherein:
   a) said mammalian SPS is a rodent or primate protein;
   b) said fragment exhibits a natural sequence;
   c) said protein exhibits selelnophosphate synthetase biological activity;
   d) said fragment is substantially a full length selenophosphate synthetase;
   e) said protein comprises a selenocysteine residue; or
   f) said fragment has a glycosylation pattern distinct from a corresponding segment of a natural selenophosphate synthetase.
3. A cell comprising an isolated protein of claim 1.
4. The protein of claim 1, wherein said mammalian selenophosphate synthetase has a sequence exhibiting at least 90% identity to SEQ ID NO 2 or 4.
5. An isolated or recombinant nucleic acid encoding a protein of claim 1 where said portion is encoded by:
   a) SEQ ID NO 1 nucleotides 129–950;
   b) SEQ ID NO 1 nucleotides 1350–1495;
   c) SEQ ID NO 3 nucleotides 139–950; or
   d) SEQ ID NO 3 nucleotides 1341–1483.
6. The nucleic acid of claim 5, wherein said nucleic acid:
   a) exhibits at least about 80% identity to a natural cDNA encoding said segment;
   b) is in an expression vector;
   c) further comprises a promotor;
   d) further comprises an origin of replication; or
   d) comprises an internal in frame termination codon which encodes a selenocysteine.
7. A cell comprising a recombinant nucleic acid of claim 5.
8. An antibody binding fragment which binds to a protein of claim 1, wherein said antibody binds to said fragment.
9. An antibody binding fragment from an antibody raised to a protein of claim 2.
10. The antibody binding fragment of claim 9, wherein said binding frangment;
    a) blocks said selenophosphate synthetase biological activity;
    b) is from a camel; or
    c) is an Fab, F(ab)$_2$, or Fv fragment.
11. A kit comprising:
    a) said protein of claim 1;
    b) a polynucleotide capable of detecting a nucleic acid encoding said protein;
    c) an antibody capable of binding to said segment of said protein.
12. A method of producing a monoselenophosphate molecule comprising the step of combining an appropriate amount of:
    a) a selenium compound;
    b) ATP; and
    c) an isolated mammalian selenophosphate synthetase.
13. A method of incorporating selenium into a selenoprotein comprising the step of combining an appropriate amount of:
    a) a selenoprotein message;
    b) selenium; and
    c) an isolated mammalian selenophosphate synthetase.
14. A product made by the method of claim 13.
15. The method of claim 13, wherein said selenium is labeled.
16. A method of screening a sample for a modulator or an analog of SPS activity comprising contacting a mammalian SPS with a sample and measuring SPS activity.
17. The method of claim 15, wherein said modulator:
    a) increases selenophosphate synthetase activity by at least about 10%;
    b) decreases selenophosphate synthetase activity by at lease about 10%;
    c) increases selenophosphate synthetase activity by at least about 20%; or
    b) decreases selenophosphate synthetase activity by at least about 20%.
18. A method of inducing selenocysteine incorporation into a protein in a cell, comprising a step of introducing a mammalian selenophosphate synthetase into a cell.

BRIEF DESCRIPTION OF THE DRAWINGS

FIG. 2 illustrates comparative analysis of the protein sequence of bacterial, mouse, and human SPS (HuSPS is human SPS; MoSPS is murine SPS; and EcSPS is *E. Coli* SPS).

DETAILED DESCRIPTION OF THE PREFERRED EMBODIMENTS

Figure 1A:
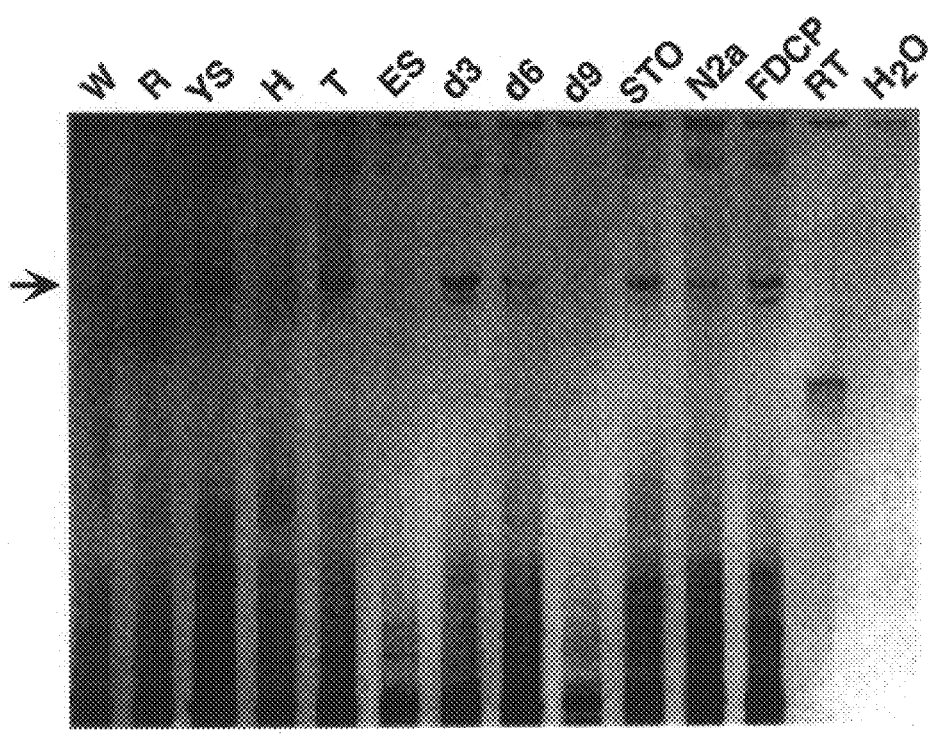
FIG. 1 shows identification of mouse SPS. A) DD-PCR and B) Northern Blot analysis of SPS expression. W—early day 8.5 embryo proper; R—late day 8.5 embryo proper; YS—day 8.5 yolk sac; H—Head primordium of day 8.0 embryos; T—Posterior region of day 8.0 embryos; ES—ES Cells; d3, d6, d9—day 3, day 6 and day 9 EBs; STO, N2a and FDCPmixA4 as described.
Figure 1B:
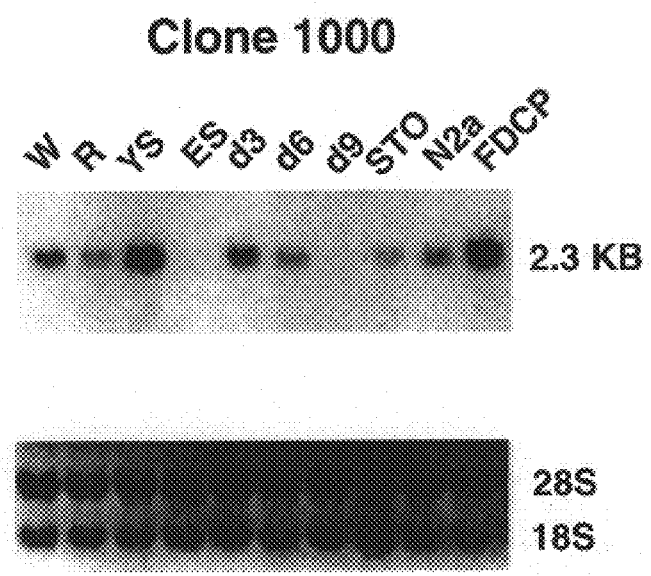
Figure 3A:
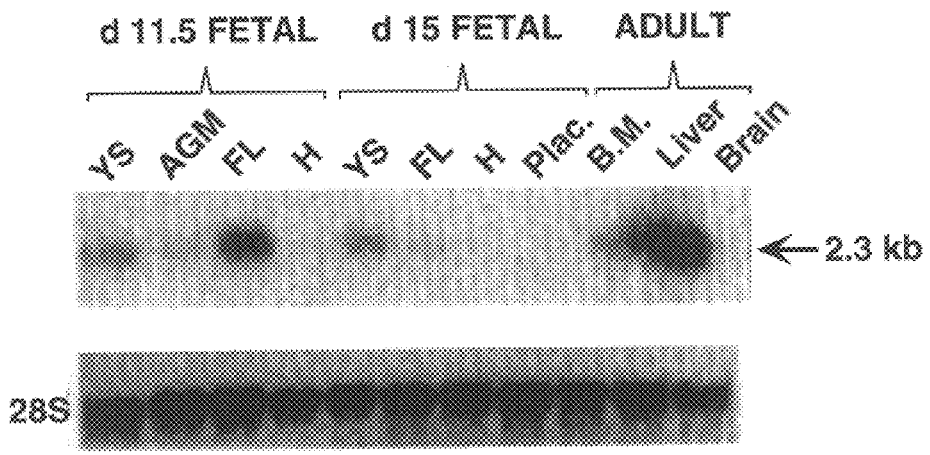
FIGS. 3A and 3B illustrate Northern Blot Analyses of the expression of SPS in various fetal and adult tissues. YS—Yolk Sac, AGM—AGM region (see text), FL—Fetal liver, H—Head of the embryo, Plac—Placenta, BM—Bone Marrow, S. Muscle—Skeletal Muscle, A. Fat—Perivisceral abdominal fat, FDCP—FDCPmixA4 cell line, STO and N2a as described in the text. 28S—ribosomal RNA.
Figure 3B:
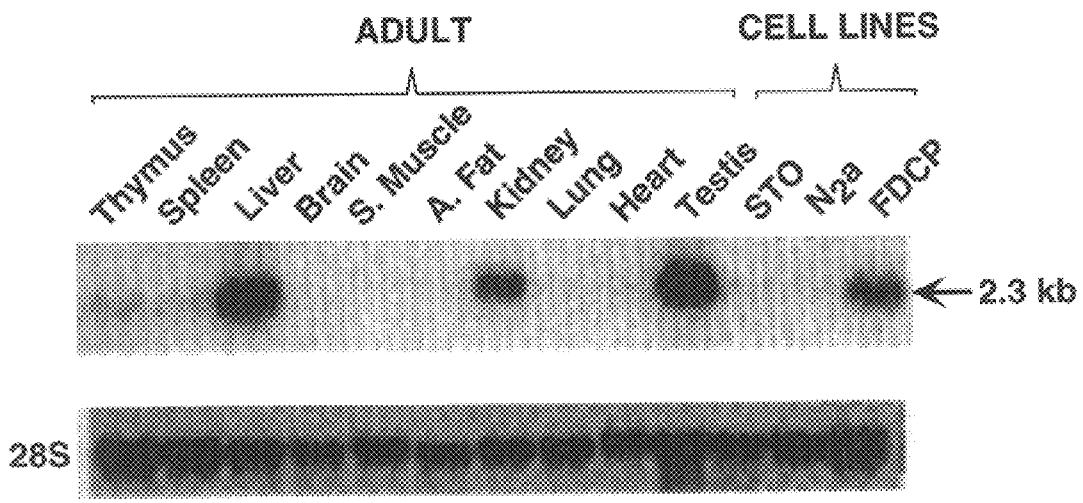

All references cited herein are incorporated herein by reference to the same extent as if each individual publication or patent application was specifically and individually indicated to be incorporated by reference.

General

The present invention provides the amino acid sequence and DNA sequences encoding various mammalian proteins which exhibit properties of catalyzing the synthesis of selenocytseine. These proteins are designated selenophosphate synthestases (SPS) because of their ability to catalyze the first step in the anabolism of selenium. The selenoproteins catalyze a biochemical reaction which ultimately result in the incorporation of a selenocysteine within a target protein or tRNA. As such SPS contitute a control point of the synthesis of mammalian selenoproteins.

Using the Differential Display by PCR (DD-PCR) technique, see, e.g., Liang, et al. (1992) *Science* 257:967–971; and Liang, et al. (1993) *Nucleics Acids Research* 21:3269–3275, a model was devised based on the comparison of patterns of gene expression between mRNA populations obtained from cells or tissues, with or without hematopoietic activity, collected from the mouse embryo, Embryoid Bodies (EBs) and from mouse cell lines. Direct comparison of gene expression in various tissues of different stage mouse embryos and cell lines of hematopoietic, fibroblast and neuronal cells led to the identification of differentially expressed mRNA populations. One PCR band, designated Clone 1000 was used to screen a cDNA library.

A cDNA library derived from the murine hematopoietic FDCPmixA4 cell line was screened by hybridization to the DD-PCR product Clone 1,000. A cDNA was isolated which, upon sequencing, was identified as encoding mouse SPS as described in bacterial organisms. Veres, et al. (1994) *J. of Biol. Chem.* 269:10597–10603. Repetitive double-strand sequencing of the full length mouse SPS cDNA confirmed the existence of a UGA codon (Codon 63) located in the open reading frame at a position corresponding to cysteine 17 in bacterial SPS. Cysteine 17 had been shown to be essential for the activity of the bacterial SPS enzyme, see, e.g., Kim, et al. (1992) *J. Biol. Chem.* 267:19650–654; and Kim, et al.(1993) *J. Biol. Chem.* 268:27020–025. A human homologue, SPS-8A, was isolated from a cDNA library derived from an activated human CD8$^+$CD4$^-$ T cell clone. A UGA codon at position 63 was also found to be present in the human clone.

Table 1 shows the comparison of the in-frame UGA codon in mouse, human and bacteria SPS.

loop features and the bulges in the 5' and the 3' sides of this stem-loop are similar to the SECIS elements described in other eukaryotic selenoproteins. See Berry, et al. (1993) *EMBO J.* 12:3315–3322. However, this putative SECIS element differs from all other eukaryotic SECIS elements for its location inside the translating region, immediately after the UGA codon, which was considered, until this report, a characteristic of bacterial SECIS elements.

Northern Blot analysis demonstrated that SPS was preferentially expressed in tissues where selenoproteins are known to be produced at higher levels: liver, see, Takahashi, et al. (1987)*Arch. Biochem. Biophys* 256:677–686; Behne, et al. (1990) *Biochem. Byophis. Res. Commun.* 173:1143–1149; and Hill, et al. (1991) *J. Biol. Chem.* 265:10060–10063; kidney, see, Behne, et al. (1990) *Biochem. Byophis. Res. Commun.* 173:1143–1149; and testis, see, Kleene, et al. (1990) *Dev. Biol.* 137:395–402; and Karimpour, et al. (1992) *DNA and Cell Biology* 11:693–699; and in the earlier stages of liver development, e.g., day 11.5 and day 15 fetal liver.

Expression of SPS mRNA is also abundant in active sites of hematopoiesis and blood cell development (yolk sac, bone marrow, spleen and thymus). This tissue distribution suggests a role for SPS in blood and immune cell biology. The expression of SPS mRNA is upregulated upon CD4$^+$ CD8$^-$ T lymphocyte activation in vitro.

Levels of SPS mRNA are higher in both Th1 and Th2 subsets of CD4+ cells in mice infected with Leischmania major than in normal non-infected mice, thus suggesting upregulation of SPS mRNA expression by a antigen-dependent stimulus in T cells.

Serum deprived fibroblasts, which are in the G0 phase of the cell cycle and therefore quiescent, have a higher expression of SPS than serum stimulated, actively dividing fibroblasts suggesting that SPS may have a role directing the production of MSP used in the synthesis of selenoproteins not directly involved in cell division but in the immune response.

```
Bacteria Gly Ala Gly Cys Gly Cys Lys Ile Ser  (corresponding to amino acids
                 |       |   |   |              14 through 22 of SEQ ID NO:5)
Mouse    Met Lys Gly TGA Gly Cys Lys Val Pro   (corresponding to nucleotides
                 |       |   |   |   |   |      315 through 341 of SEQ ID NO:1)
Human    Met Lys Gly TGA Gly Cys Lys Val Pro   (corresponding to nucleotides
                                                307 through 333 of SEQ ID NO:3)
```

In order to demonstrate that SPS contained a selenocysteine encoded by UGA codon 63, COS-7 cells were transfected with an expression vector (PME18X) containing the SPS translating region. A tag (FLAG) sequence was introduced between the first and second aminoacids of SPS. The FLAG peptide sequence would allow the detection of the SPS-FLAG protein by Western Blotting using an anti-FLAG antibody. A construct was also made in which the UGA codon (Codon 63) was mutated into a UGC codon. This would result in a replacement of cysteine for selenocysteine and this mutant form of SPS was designated CYS mutant. This construct was independently transfected into COS-7 cells. Finally, COS-7 cells were independently transfected with PME18X plasmid without insert.

All selenoproteins previously described in eukaryotes require the 3' untranslated region of their respective mRNA or cDNA to be present for the incorporation of selenocysteine and the readthrough of the UGA codon to occur. However, both mouse and human SPS cDNAs contain a RNA secondary structure located inside their translating region that resembles a SECIS element. The size, structure, The protein for SPS should be present in the mentioned tissue types and the interaction of the protein with a target protein or tRNA should be important for mediating various aspects of cellular physiology or development. The distribution of the SPS protein in different tissues suggests that it has functional roles outside the immune system, e.g., in developmental regulation in other cell types. See, e.g., Gilbert (1991) *Developmental Biology* (3d ed.), Sinauer Associates, Sunderland, Mass.; Browder, et al. (1991) *Developmental Biology* (3d ed.), Saunders, Philadelphia, Pa.; Russo, et al. (1992) *Development: The Molecular Genetic Approach,* Springer-Verlag, New York, N.Y.; and Wilkins (1993) *Genetic Analysis of Animal Development* (2d ed.), Wiley-Liss, New York, N.Y.

Purified SPS Protein

Mouse and human SPS amino acid sequences are shown in Table 2, also referred to in SEQ ID NO: 2, and 4, respectively. These amino acid sequences, provided amino to carboxy, are important in providing sequence information in the synthetase allowing for distinguishing the protein from other proteins. Moreover, the peptide sequences allow preparation of peptides to generate antibodies to recognize such segments, and allow preparation of oligonucleotide probes, both of which are strategies for isolation, e.g., cloning, of genes encoding such sequences. In particular, the invention provides various fragments of different lengths with all combinations of endpoints, which can be useful, e.g., as immunogenic polypeptides.

Table 2: Mouse and Human SPS sequences. The nucleic acid sequence of cDNA isolates are provided above the translation product, using the standard genetic code. Note, however, that each protein contains an internal UAG termination codon which is normally translated into the unusual selenocysteine.

TABLE 2

Mouse and Human SPS sequences. The nucleic acid sequence of cDNA isolates are provided above the translation product, using the standard genetic code. Note, however, that each protein contains an internal UAG termination codon which is normally translated into the usual selenocysteine.

```
Mouse SelenoPhosphate Synthesis (SEQ ID NO: 1 and 2) from: 1 to: 2202
     cggacGtgGgCGAGTCCTCCGGTCCGGCTcGcGTGGTTGATCATCTCCTGGcGTAACCTT
   1 ---------+---------+---------+---------+---------+---------+    60

GGcCCGCTGTGGCTGGGAGACTCATCTGCAGGTATCTGGGCCTTCTGGTCCGCACGGCCT
  61 ---------+---------+---------+---------+---------+---------+   120

CCCGGGCGAGCGGCGCGATGGCGGAAGCGGCGGCGGCGGGCGCCAGCGGAGAAACCATGG
 121 ---------+---------+---------+---------+---------+---------+   180
                          M  A  E  A  A  A  A  G  A  S  G  E  T  M  A

CgGCGCTAGTGGCcGCAGAAGGTTCCTTGGGCCCGGCGGGCTGGTCTGCCGGcCGGAGTT
 181 ---------+---------+---------+---------+---------+---------+   240
      A  L  V  A  A  E  G  S  L  G  P  A  G  W  S  A  G  R  S  F

TCTCCAACTACCGGCCGTTCGAGCCCCAGACACTGGGCTTCAGCCCGAGCTGGCGGCTGA
 241 ---------+---------+---------+---------+---------+---------+   300
        S  N  Y  R  P  F  E  P  Q  T  L  G  F  S  P  S  W  R  L  T

CGAGCTTCTCCGGCATGAAGGGCTGAGGCTGCAAGGTCCCCAGGAGACCCTGCTCAAAC
 301 ---------+---------+---------+---------+---------+---------+   360
        S  F  S  G  M  K  G  *  G  C  K  V  P  Q  E  T  L  L  K  L

TCCTGGAGGGACTGACGCGGCCCGCGCTGCAGCCCCCGCTTACCTCGGGTCTGGTCGGGG
 361 ---------+---------+---------+---------+---------+---------+   420
        L  E  G  L  T  R  P  A  L  Q  P  P  L  T  S  G  L  V  G  G

GCCAGGAAGAGACGGTGCAGGAAGGGGGCCTGTCCACCAGGCCCGGCCCCGGCTCAGCCT
 421 ---------+---------+---------+---------+---------+---------+   480
        Q  E  E  T  V  Q  E  G  G  L  S  T  R  P  G  P  G  S  A  F

TCCCCTCGCTGAGCATTGGCATGGACTCCTGCGTCATCCCCCTGAGGCACGGAGGCCTGT
 481 ---------+---------+---------+---------+---------+---------+   540
        P  S  L  S  I  G  M  D  S  C  V  I  P  L  R  H  G  G  L  S

CGCTGGTGCAGACCACCGACTTCTTTTACCCCTTGGTGGAAGATCCCTATATGATGGGGC
 541 ---------+---------+---------+---------+---------+---------+   600
        L  V  Q  T  T  D  F  F  Y  P  L  V  E  D  P  Y  M  M  G  R

GCATAGCTTGTGCCAATGTGCTCAGTGACCTCTATGCCATGGGTATCACTGAGTGTGACA
 601 ---------+---------+---------+---------+---------+---------+   660
        I  A  C  A  N  V  L  S  D  L  Y  A  M  G  I  T  E  C  D  N

ACATGTTGATGTTACTCAGTGTGAGCCAGAGCATGAGTGAAAAGGAACGAGAGAAGGTGA
 661 ---------+---------+---------+---------+---------+---------+   720
        M  L  M  L  L  S  V  S  Q  S  M  S  E  K  E  R  E  K  V  T

CACCGCTCATGATCAAAGGCTTTCGTGACGCTGCGGAGGAGGGAGGCACTGCAGTGACCG
 721 ---------+---------+---------+---------+---------+---------+   780
        P  L  M  I  K  G  F  R  D  A  A  E  E  G  G  T  A  V  T  G

GTGGACAGACAGTGGTCAACCCGTGGATTATCATCGGTGGCGTTGCCACGGTGGTGTGTC
 781 ---------+---------+---------+---------+---------+---------+   840
        G  Q  T  V  V  N  P  W  I  I  I  G  G  V  A  T  V  V  C  Q

AGCAAAATGAATTCATAATGCCTGATAGTGCCGTGGTAGGAGATGTGCTGGTATTAACCA
 841 ---------+---------+---------+---------+---------+---------+   900
        Q  N  E  F  I  M  P  D  S  A  V  V  G  D  V  L  V  L  T  K

AACCTTTAGGAACCCAGGTTGCTGCCAATGCCCACCAATGGCTGGATAATCCTGAGAAAT
 901 ---------+---------+---------+---------+---------+---------+   960
```

TABLE 2-continued

Mouse and Human SPS sequences. The nucleic acid sequence of cDNA isolates are provided above the translation product, using the standard genetic code. Note, however, that each protein contains an internal UAG termination codon which is normally translated into the usual selenocysteine.

```
          P   L   G   T   Q   V   A   A   N   A   H   Q   W   L   D   N   P   E   K   W   -
     GGAATAAAATCAAGATGGTGGTTTCCAGAGAGGAAGTAGAGTTAGCCTATCAGGAAGCTA
 961 ---------+---------+---------+---------+---------+---------+ 1020
          N   K   I   K   M   V   V   S   R   E   E   V   E   L   A   Y   Q   E   A   M   -

TGTtCAATATGGCTACTCTAAACAGGACTGCTGCTGGCTTGATGCACACTTTTAATGCCC
1021 ---------+---------+---------+---------+---------+---------+ 1080
          F   N   M   A   T   L   N   R   T   A   A   G   L   M   H   T   F   N   A   H   -

ACGCAGCCACGGATATCACAGGCTTTGGCATATTAGGACACTCTCAGAACCTGGCAAAAC
1081 ---------+---------+---------+---------+---------+---------+ 1140
          A   A   T   D   I   T   G   F   G   I   L   G   H   S   Q   N   L   A   K   Q   -

AGCAAAAAAATGAAGTGTCCTTTGTCATACATAAtCTGCCAATAATTGCCAAGATGGCTG
1141 ---------+---------+---------+---------+---------+---------+ 1200
          Q   K   N   E   V   S   F   V   I   H   N   L   P   I   I   A   K   M   A   A   -

CGATCAGCAAAGCCAGTGGGCGCTTTGGCCTCCTCCAAGGAACGTCAGCTGAAACCTCTG
1201 ---------+---------+---------+---------+---------+---------+ 1260
          I   S   K   A   S   G   R   F   G   L   L   Q   G   T   S   A   E   T   S   G   -

GGGGATTACTGATTTGTCTGCCAAGAGAGCAGGCGGCCCGCTTTTGTTCGGAAATCAAAT
1261 ---------+---------+---------+---------+---------+---------+ 1320
          G   L   L   I   C   L   P   R   E   Q   A   A   R   F   C   S   E   I   K   S   -

CTTCCAAGTACGGAGAGGGTCACCAAGCTTGGATCGTTGGCATCGTGGAGAAGGGAAACC
1321 ---------+---------+---------+---------+---------+---------+ 1380
          S   K   Y   G   E   G   H   Q   A   W   I   V   G   I   V   E   K   G   N   R   -

GGACAGCCCGGATCATTGACAAGCCTCGCGTTATTGAAGTTCTACCTCGGGGAGCCTCTG
1381 ---------+---------+---------+---------+---------+---------+ 1440
          T   A   R   I   I   D   K   P   R   V   I   E   V   L   P   R   G   A   S   A   -

CTGCTGCTGCTGCTGCTCCTGATAATTCCAACGCAGCCTCTGAGCCTAGTTCTTGAAATG
1441 ---------+---------+---------+---------+---------+---------+ 1500
          A   A   A   A   A   P   D   N   S   N   A   A   S   E   P   S   S   *           -

GAATAGCGGTTGTTGGGAACtCGGAGCCATTCTACCCGCTCAGGGACTGCTGGCCAGGGT
1501 ---------+---------+---------+---------+---------+---------+ 1560
                                                                        -

TGATTTTAAGACCTTTCCAAAGGCTGCTTGCATGGTTCCTCCAGGCCCATCCAAAGCTTC
1561 ---------+---------+---------+---------+---------+---------+ 1620
                                                                        -

CTGTATGTGCATCCAGGCCTGTGAGTAATGGCGCTGCGGATGTGTGTTCATCTGTTGAGA
1621 ---------+---------+---------+---------+---------+---------+ 1680
          V   C   A   S   R   P   V   S   N   G   A   A   D   V   C   S   S   V   E   S   -

GCATGAGGAGCAAAAACCCGTTTCCCAAAGCAAGAGGAGGCTATTTCAGTTTTAGGGATT
1681 ---------+---------+---------+---------+---------+---------+ 1740
                                                                        -

TTTTTTTTTTTTTTTTTTGCACTGAGTTGATTCATTTCTGCACAGGGAGTAAAGATTAT
1741 ---------+---------+---------+---------+---------+---------+ 1800
                                                                        -

TAAGAtTACATATGAGAAAAGTAAACCTGCAACATGAAAAATTATTTGGACCAATATATT
1801 ---------+---------+---------+---------+---------+---------+ 1860
                                                                        -

GATAAATCTAAATTGTTAGGAGAACTCTTACTGATTTATTGTCAAATTTGTTATTAATTT
1861 ---------+---------+---------+---------+---------+---------+ 1920
                                                                        -

TTTTCTGAGAAACTGCCTCTTTTCCTGTTCTGGACAAGAGTTGAGCAGCTTGTCCGacag
1921 ---------+---------+---------+---------+---------+---------+ 1980
                                                                        - gaAAGGAAGACTAGCCACCTGACTTGGTCTCTGATAATGATGTCTCTCCCTCTAACTCCC
1981 ---------+---------+---------+---------+---------+---------+ 2040
                                                                        -
```

TABLE 2-continued

Mouse and Human SPS sequences. The nucleic acid sequence of cDNA isolates are provided above the translation product, using the standard genetic code. Note, however, that each protein contains an internal UAG termination codon which is normally translated into the usual selenocysteine.

```
       AGTAAGGACTGGGAGAGGCTGAACAAACCTCAGAGCCAGGTGTCGGTGGCCATTGAATCT
2041   ---------+---------+---------+---------+---------+---------+   2100

TACACTGAAACTTCTGGAGATTTAATTAATAAAGAgAAtttcttACaGTAActAAAtAAA
2101   ---------+---------+---------+---------+---------+---------+   2160

AgggctttgttggAAAAAAAAaaaaaaaaaaaaaaaaaaaaa
2161   ---------+---------+---------+---------+--                      2202
```

Human SelenoPhosphate Synthetase from: 1 to: 1932
```
       GTGCATGCCGTGGGTCTGACGGCTTGAGTAGCGCTAGGGAGAATCCCTGCAGGTAATATT
   1   ---------+---------+---------+---------+---------+---------+     60

TGACTTTTGCTTCATATTAAtCTGAGTGGAAAATAAAAGGGCCCTCTTCTCCTCTCGCTT
  61   ---------+---------+---------+---------+---------+---------+    120

CCCTGCCGGGCAGGCGCCATGGCGGAAGCCTCGGCGACGGGCGCCTGCGGAGAGGCGATG
 121   ---------+---------+---------+---------+---------+---------+    180
                         M   A   E   A   S   A   T   G   A   C   G   E   A   M

GCAGCGGCGGAAGGCTCCTCGGGcccggcgggcttgactctgggccggagcttctcgaac
 181   ---------+---------+---------+---------+---------+---------+    240
        A   A   A   E   G   S   S   G   P   A   G   L   T   L   G   R   S   F   S   N taccggcCCTTCGAGCCCCAGgcgttgggcctcagcccgagctggcggctgacgggcttc
 241   ---------+---------+---------+---------+---------+---------+    300
        Y   R   P   F   E   P   Q   A   L   G   L   S   P   S   W   R   L   T   G   F tccggcatgaagggctgaggctgcaaggtcccgcaggaggCGCTGCTCAAACTCCTGGCG
 301   ---------+---------+---------+---------+---------+---------+    360
        S   G   M   K   G   *   G   C   K   V   P   Q   E   A   L   L   K   L   L   A GGACTGACGCGGCCGGACGTGCGGCCCCCGCTGGGCCGGGGCCTGGTGGGTGGCCAGGAA
 361   ---------+---------+---------+---------+---------+---------+    420
        G   L   T   R   P   D   V   R   P   P   L   G   R   G   L   V   G   G   Q   E GAGGCGTCCCAGGAAGCCGGCCTGCCGGCAGGAGCGGGCCCCAGCCCCACCTTTCCAGCC
 421   ---------+---------+---------+---------+---------+---------+    480
        E   A   S   Q   E   A   G   L   P   A   G   A   G   P   S   P   T   F   P   A CTGGGCATCGGGATGGACTCCTGCGTCATCCCCCTGAGGCACGGGGGCCTGTCACTGGTG
 481   ---------+---------+---------+---------+---------+---------+    540
        L   G   I   G   M   D   S   C   V   I   P   L   R   H   G   G   L   S   L   V CAGACCACGGACTTCTTTTACCCCTTGGTAGAAGATCCCTACATGATGGGGCGCATAGCT
 541   ---------+---------+---------+---------+---------+---------+    600
        Q   T   T   D   F   F   Y   P   L   V   E   D   P   Y   M   M   G   R   I   A TGTGCCAACGTGCTGAGTGACCTCTACGCCATGGGGATTACTGAGTGTGACAACATGTTG
 601   ---------+---------+---------+---------+---------+---------+    660
        C   A   N   V   L   S   D   L   Y   A   M   G   I   T   E   C   D   N   M   L ATGTTACTCAGCGTCAGCCAGAGTATGAGTGAGGAGGaACgCGAAAAGGTaACGCCACTC
 661   ---------+---------+---------+---------+---------+---------+    720
        M   L   L   S   V   S   Q   S   M   S   E   E   E   R   E   K   V   T   P   L ATGGTCAAAGGCTTtCGGGATGCGGCTGAGGAAGGAGGGACGGCAGTGACCGGTGGGCAA
 721   ---------+---------+---------+---------+---------+---------+    780
        M   V   K   G   F   R   D   A   A   E   E   G   G   T   A   V   T   G   G   Q ACGGTGGTCAACCCTTGGATTATAATCGGTGGAGTTGCCACTGTAGTATGCCAACCAAAT
 781   ---------+---------+---------+---------+---------+---------+    840
        T   V   V   N   P   W   I   I   I   G   G   V   A   T   V   V   C   Q   P   N GAGTTCATAATGCCGGACAGCGCCGTCGTTGGGGACGTGCTGGTGTTAACCAAACCGTTA
 841   ---------+---------+---------+---------+---------+---------+    900
        E   F   I   M   P   D   S   A   V   V   G   D   V   L   V   L   T   K   P   L
```

TABLE 2-continued

Mouse and Human SPS sequences. The nucleic acid sequence of cDNA isolates are provided above the translation product, using the standard genetic code. Note, however, that each protein contains an internal UAG termination codon which is normally translated into the usual selenocysteine.

```
        GGAACCCAGGTTGCTGTCAATGCCCACCAATGGCTGGATAATCCTGAAAGATGGAATAAA
 901    ---------+---------+---------+---------+---------+---------+    960
          G  T  Q  V  A  V  N  A  H  Q  W  L  D  N  P  E  R  W  N  K

GTAAAGATGGTGGTCTCCAGAGAAGAGGTGGAGCTGGCCTATCAGGAAGCCATGTTCAAT
 961    ---------+---------+---------+---------+---------+---------+   1020
          V  K  M  V  V  S  R  E  E  V  E  L  A  Y  Q  E  A  M  F  N

ATGGCTACCCTCAACAGAACTGCTGCAGGTTTAATGCACACATTTAATGCCCATGCGGCC
1021    ---------+---------+---------+---------+---------+---------+   1080
          M  A  T  L  N  R  T  A  A  G  L  M  H  T  F  N  A  H  A  A

ACAGATATCACAGGCTTTGGCATTCTAGGACACTCCCAGAACCTTGCAAAACAACAAAGA
1081    ---------+---------+---------+---------+---------+---------+   1140
          T  D  I  T  G  F  G  I  L  G  H  S  Q  N  L  A  K  Q  Q  R

AATGAAGTGTCCTTTGTTATTCATAATCTGCCAATAATTGCCAAGATGGCTGCCGTCAGC
1141    ---------+---------+---------+---------+---------+---------+   1200
          N  E  V  S  F  V  I  H  N  L  P  I  I  A  K  M  A  A  V  S

AAGGCCAGTGGACGGTTTGGGCTTCTTCAAGGAACCTCAGCTGAAACCTCTGGGGATTA
1201    ---------+---------+---------+---------+---------+---------+   1260
          K  A  S  G  R  F  G  L  L  Q  G  T  S  A  E  T  S  G  G  L

CTGATTTGTCTGCCAAGAGAACAGGCgGCTCGCTTTTGTTCTGAAATCAAATCCTCCAAG
1261    ---------+---------+---------+---------+---------+---------+   1320
          L  I  C  L  P  R  E  Q  A  A  R  F  C  S  E  I  K  S  S  K

TACGGAGAGGGTCACCAAGCGTGGATCGTTGGCATTGTGGAAAAGGGAAACCGAACGGCC
1321    ---------+---------+---------+---------+---------+---------+   1380
          Y  G  E  G  H  Q  A  W  I  V  G  I  V  E  K  G  N  R  T  A

CGGATCATTGACAAGCCGCGAGTTATTGAAGTCCTGCCTCGTGGGGCCACAGCTGCTGTT
1381    ---------+---------+---------+---------+---------+---------+   1440
          R  I  I  D  K  P  R  V  I  E  V  L  P  R  G  A  T  A  A  V

CTTGCTCCTGACAGTtCAAATGCCTCCTCTGAGCCTAGCTCGTGAGATGAAAGAACAGAA
1441    ---------+---------+---------+---------+---------+---------+   1500
          L  A  P  D  S  S  N  A  S  S  E  P  S  S  *

GTTGTTTGGACCTTAGAGCCATTGTCCACAATCACGGATGGTTCTCAAGAGTTGATTGTA
1501    ---------+---------+---------+---------+---------+---------+   1560

AGAAATTTCCAAAGAAGGCTGCCTGCATAGTGGTTCCGGCTGCCCTTtctaggtgattgg
1561    ---------+---------+---------+---------+---------+---------+   1620 aatcagcccatctaaagcagtctttatatgcattccgaggccagagtaacattttgaact
1621    ---------+---------+---------+---------+---------+---------+   1680 ttgggggatatttgttcatcacttGGGTAGAAGAGGAGCAAAAATACTTCTGTTTTCTC
1681    ---------+---------+---------+---------+---------+---------+   1740

TTGCCAAAGTAAGATGAAGCTATTCCAGGTTGAGGGATTTTTCTTTgcncggggttgatt
1741    ---------+---------+---------+---------+---------+---------+   1800 aatttctgcacagggagtgagattattaaagtaacacacacacaaagtaaattgcaaaat
1801    ---------+---------+---------+---------+---------+---------+   1860 gaaaaaattagaagcaaatgagttttggaccaatattgttgataaatctaaattgttaa
1861    ---------+---------+---------+---------+---------+---------+   1920 gagagatcttat
1921    ---------+--                                                   1932
```

As used herein, the term "mouse SPS" shall encompass, when used in a protein context, a protein having mouse amino acid sequences shown in SEQ ID NO: 2, or a significant fragment of such a protein. The term "human SPS" shall emcompass, when used in a protein context, a protein having a human amino acid sequence shown in SEQ ID NO: 4. It also refers to a mouse or human derived polypeptide which exhibits similar biological function to mouse or human SPS, respectively.

The invention also provides binding components, e.g., antibodies, which typically bind to an SPS with high affinity, e.g., at least about 100 nM, usually better than about 30 nM, preferably better than about 10 nM, and more preferably at better than about 3 nM. Homologous proteins would be found in mammalian species other than mouse or humans, e.g., rats. Non-mammalian species should also possess structurally or functionally related genes and proteins.

The term "polypeptide" as used herein includes a significant fragment or segment, and encompasses a stretch of amino acid residues of at least about 8 amino acids, generally at least about 12 amino acids, typically at least about 16 amino acids, preferably at least about 20 amino acids, and, in particularly preferred embodiments, at least about 30 or more amino acids.

The term "binding composition" refers to molecules that bind with specificity to SPS, e.g., in an antibody-antigen interaction. It also includes compounds, e.g., proteins, which specifically associate with SPS, including in a natural physiologically relevant protein-protein interaction, either covalent or non-covalent. The molecule may be a polymer, or chemical reagent. A functional analog may be a protein with structural modifications, or may be a molecule, which has a molecular shape which interacts with the appropriate binding determinants.

Substantially pure typically means that the protein is free from other contaminating proteins, nucleic acids, and other biologicals derived from the original source organism, e.g., the natural source. Purity may be assayed by standard methods, typically by weight, and will ordinarily be at least about 40% pure, generally at least about 50% pure, often at least about 60% pure, typically at least about 80% pure, preferably at least about 90% pure, and in most preferred embodiments, at least about 95% pure. Typical means to assess purity include gel staining, either coomassie blue or silver staining.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. For diagnostic purposes, the temperature will usually be about room temperature or warmer, but less than the denaturation temperature of components in the assay. For therapeutic purposes, the temperature will usually be body temperature, typically about 37° C. for humans and mice, though under certain situations the temperature may be raised or lowered in situ or in vitro.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates natural lipid bilayer interactions. In certain embodiments, the denatured protein will be useful, e.g., in raising antibodies.

The solvent and electrolytes will usually be a biologically compatible buffer, of a type used for preservation of biological activities, and will usually approximate a physiological aqueous solvent. Usually the solvent will have a neutral pH, typically between about 5 and 10, and preferably about 7.5. On some occasions, one or more detergents will be added, typically a mild non-denaturing one, e.g., CHS or CHAPS, or a low enough concentration as to avoid significant disruption of structural or physiological properties of the protein.

Physical Variants

This invention also encompasses proteins or peptides having substantial amino acid sequence identity with the amino acid sequence of the SPS. The variants include species or allelic variants.

Amino acid sequence homology, or sequence identity, is determined by optimizing residue matches, if necessary, by introducing gaps as required. See also Needleham, et al. (1970) *J. Mol. Biol.* 48:443–453; Sankoff, et al. (1983) Chapter One in *Time Warps, String Edits, and Macromolecules: The Theory and Practice of Sequence Comparison*, Addison-Wesley, Reading, Mass.; and software packages from IntelliGenetics, Mountain View, Calif.; and the University of Wisconsin Genetics Computer Group, Madison, Wis.;. Seqeunce identity changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences are typically intended to include natural allelic and interspecies variations in each respective protein sequence. Typical homologous proteins or peptides will have from 25–100% identity (if gaps can be introduced), to 50–100% identity (if conservative substitutions are included) with the amino acid sequence of the SPS protein. Identity measures will be at least about 35%, generally at least about 40%, often at least about 50%, typically at least about 60%, usually at least about 70%, preferably at least about 80%, and more preferably at least 90%.

The isolated SPS DNA can be readily modified by nucleotide substitutions, nucleotide deletions, nucleotide insertions, and inversions of nucleotide stretches. These modifications result in novel DNA sequences which encode these antigens, their derivatives, or proteins having similar physiological, immunogenic, antigenic, or other functional activity. These modified sequences can be used to produce mutant antigens or to enhance expression. Enhanced expression may involve gene amplification, increased transcription, increased translation, and other mechanisms. "Mutant SPS" encompasses a polypeptide otherwise falling within the sequence identity definition of the mouse or human SPS as set forth above, but having an amino acid sequence which differs from that of SPS as normally found in nature, whether by way of deletion, substitution, or insertion. This generally includes proteins having significant identity with a protein or polypeptide portion having sequences of SEQ ID NO: 2 or 4, and may share various biological activities, e.g., antigenic or immunogenic, with those sequences, and in preferred embodiments contain most of the disclosed sequences. Similar concepts apply to different SPS proteins, particularly those found in various warm blooded animals, e.g., mammals and birds. These descriptions are generally meant to encompass all SPS proteins, not limited to the mouse or human embodiments specifically described.

SPS mutagenesis can also be conducted by making amino acid insertions or deletions. Substitutions, deletions, insertions, or any combinations may be generated to arrive at a final construct. Insertions include amino- or carboxy-terminal fusions. Random mutagenesis can be conducted at a target codon and the expressed mutants can then be screened for the desired activity. Methods for making substitution mutations at predetermined sites in DNA having a known sequence are well known in the art, e.g., by M13 primer mutagenesis or polymerase chain reaction (PCR) techniques. See, e.g., Sambrook, et al. (1989); Ausubel, et al. (1987 and Supplements); and Kunkel, et al. (1987) *Meth. Enzymol.* 154:367–382.

The present invention also provides recombinant proteins, e.g., heterologous fusion proteins using segments from these proteins. A heterologous fusion protein is a fusion of proteins or segments which are naturally not normally fused in the same manner. A similar concept applies to heterologous nucleic acid sequences.

In addition, new constructs may be made from combining similar functional domains from other proteins. For example, protein-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992.

The phosphoramidite method described by Beaucage and Carruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence, e.g., PCR techniques.

Functional Variants

The blocking of physiological response to SPS may result from the inhibition of synthetase activity. Thus, in vitro assays of the present invention will often use isolated protein, membranes from cells containing a recombinant bound SPS protein, soluble fragments, or fragments attached to solid phase substrates. These assays will also allow for the diagnostic determination of the effects of either binding segment mutations and modifications, or protein mutations and modifications, e.g., protein analogs.

This invention also contemplates the use of competitive drug screening assays, e.g., where neutralizing antibodies to antigen are used, or competition of a test compound with, e.g., a natural reactant, for binding to the protein.

"Derivatives" of SPS antigens include amino acid sequence mutants, glycosylation variants, and covalent or aggregate conjugates with other chemical moieties. Covalent derivatives can be prepared by linkage of functionalities to groups which are found in SPS amino acid side chains or at the N- or C-termini, by standard means. See, e.g., Lundblad and Noyes (1988) *Chemical Reagents for Protein Modification,* vols. 1–2, CRC Press, Inc., Boca Raton, Fla.; Hugli (ed.) (1989) *Techniques in Protein Chemistry,* Academic Press, San Diego, Calif.; and Wong (1991) *Chemistry of Protein Conjugation and Cross Linking,* CRC Press, Boca Raton, Fla.

In particular, glycosylation alterations are included, e.g., made by modifying the glycosylation patterns of a polypeptide during its synthesis and processing, or in further processing steps. See, e.g., Elbein (1987) *Ann. Rev. Biochem.* 56:497–534. Also embraced are versions of the peptides with the same primary amino acid sequence which have other minor modifications, including phosphorylated amino acid residues, e.g., phosphotyrosine, phosphoserine, or phosphothreonine. Clearly the selenocysteine is a natural, but rare, amino acid incorporated into the protein. Other more common natural amino acid substitutions are contemplated, particularly at the position of the normal termination codon.

Fusion polypeptides between SPS and other homologous or heterologous proteins are also provided. Many growth factors and cytokines are homodimeric entities, and a repeat construct may have various advantages, including lessened susceptibility to proteolytic cleavage. Typical examples are fusions of a reporter polypeptide, e.g., luciferase, with a segment or domain of a protein, so that the presence or location of the fused protein may be easily determined. See, e.g., Dull, et al., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

Fusion peptides will typically be made by either recombinant nucleic acid methods or by synthetic polypeptide methods. Techniques for nucleic acid manipulation and expression are described generally, e.g., in Sambrook, et al. (1989) *Molecular Cloning: A Laboratory Manual* (2d ed.), vols. 1–3, Cold Spring Harbor Laboratory; and Ausubel, et al. (eds.) (1993) *Current Protocols in Molecular Biology,* Greene and Wiley, NY. Techniques for synthesis of polypeptides are described, e.g., in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach,* IRL Press, Oxford; and Grant (1992) *Synthetic Peptides: A User's Guide,* W. H. Freeman, NY.

This invention also contemplates the use of derivatives of SPS other than variations in amino acid sequence or glycosylation. Such derivatives may involve covalent or aggregative association with chemical moieties. Covalent or aggregative derivatives will be useful as immunogens, as reagents in immunoassays. An SPS protein can be immobilized by covalent bonding to a solid support such as cyanogen bromide-activated SEPHAROSE, by methods which are well known in the art, or adsorbed onto polyolefin surfaces, with or without glutaraldehyde cross-linking, for use in the assay or purification of anti-SPS protein antibodies. The SPS can also be labeled with a detectable group, for use in diagnostic assays, including radioactive selenium. Purification of SPS may be effected by immobilized antibodies.

A solubilized SPS or fragment of this invention can be used as an immunogen for the production of antisera or antibodies specific for the protein or fragments thereof. Purified protein can be used to screen monoclonal antibodies, encompassing antigen binding fragments of natural antibodies. Purified SPS can also be used as a reagent to detect antibodies generated in response to the presence of elevated levels of the protein or cell fragments containing the protein, both of which may be diagnostic of an abnormal or specific physiological or disease condition. This invention contemplates antibodies raised against amino acid sequences encoded by nucleotide sequences shown in SEQ ID NO: 2 or 4, or fragments of proteins containing them. In particular, this invention contemplates antibodies having binding affinity to or being raised against specific fragments which are predicted to lie outside of the lipid bilayer.

The present invention contemplates the isolation of additional closely related species variants. Southern and Northern blot analysis will establish that similar genetic entities exist in other mammals. It is likely that SPS is widespread in species variants, e.g., rodents, lagomorphs, carnivores, artiodactyla, perissodactyla, and primates.

The invention also provides means to isolate a group of related antigens displaying both distinctness and similarities in structure, expression, and function. Elucidation of many of the physiological effects of the proteins will be greatly accelerated by the isolation and characterization of distinct species variants of the proteins. In particular, the present invention provides useful probes for identifying additional homologous genetic entities in different species.

The isolated genes will allow transformation of cells lacking expression of a corresponding SPS, e.g., either species types or cells which lack corresponding proteins and exhibit negative background activity. In particular, the introduction into a cell of the selenophosphate can provide the reactants which allow production of the modified tRNA which is needed for the expression of selenoproteins. As such, the invention provides the means to incorporate selenocysteine into selenoproteins at much higher efficiency. By intorducing such reagents into a system where selenoprotein messages normally will be terminated due to termination codons within the message, the modified tRNAS will alow for the suppression of the regulatory block. This will allow for the expression of selenoproteins which are otherwise tightly regulated. The present invention provides for the means to further study and identify other proteins whose existence have remained hidden from discovery.

Dissection of critical structural elements which effect the various differentiation functions provided by proteins is possible using standard techniques of modern molecular biology, particularly in comparing members of the related class. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390.

The specific segments of interaction of SPS with other intracellular components may be identified by mutagenesis or direct biochemical means, e.g., cross-linking or affinity methods. Structural analysis by crystallographic or other physical methods will also be applicable. Further investigation of the mechanism of regulation of both enzyme activity and expression will include study of associated components which may be isolatable by affinity methods or by genetic means, e.g., complementation analysis of mutants.

Further study of the expression and control of SPS will be pursued. The controlling elements associated with the proteins may exhibit differential developmental, tissue specific, or other expression patterns. Upstream or downstream genetic regions, e.g., control elements, are of interest. In particular, developmental or physiological variants have been found. See, e.g., SEQ ID NO: 2 or 4. Differential splicing of message may lead to membrane bound forms, soluble forms, and modified versions of the protein.

Structural studies of the synthetase will lead to design of new synthetases, particularly analogs exhibiting desireable properties. This can be combined with previously described screening methods to isolate proteins exhibiting desired spectra of activities.

Antibodies

Antibodies can be raised to various SPS, including species or allelic variants, and fragments thereof, both in their naturally occurring forms and in their recombinant forms. Additionally, antibodies can be raised to SPS in either their active forms or in their inactive forms. Anti-idiotypic antibodies are also contemplated.

Antibodies, including binding fragments and single chain versions, against predetermined fragments of the proteins can be raised by immunization of animals with conjugates of the fragments with immunogenic proteins. For example, some camel heavy chain immunogloblins lack the light chain counterpart of normal immunoglobulins. See, e.g., Hamers-Casterman, et al. (1993) *Nature* 363:446–448; and Muyldermans, et al. (1994) *Prot. Engg.* 7:1129–1135. Thus, antibodies possessing only $V_H$ regions can have affinity for binding which is physiologically useful. Monoclonal antibodies are prepared from cells secreting the desired antibody, e.g., by standard methods. These antibodies can be screened for binding to normal or defective SPS, or screened for agonistic or antagonistic activity, e.g., upregulation or downregulation of the production of selenocysteine. These monoclonal antibodies will usually bind with at least a $K_D$ of about 1 mM, more usually at least about 300 $\mu$M, typically at least about 100 $\mu$M, more typically at least about 30 $\mu$M, preferably at least about 10 $\mu$M, and more preferably at least about 3 $\mu$M or better.

The antibodies of this invention can also be useful in diagnostic applications. As capture or non-neutralizing antibodies, they can be screened for ability to bind to the antigens without inhibiting binding by a second antibody. As neutralizing antibodies, they can be useful in competitive binding assays. They will also be useful in detecting or quantifying SPS protein or its target proteins. See e.g., Chan (ed.) (1987) *Immunology: A Practical Guide,* Academic Press, Orlando, Fla.; Price and Newman (eds.) (1991) *Principles and Practice of Immunoassay,* Stockton Press, N.Y.; and Ngo (ed.) (1988) *Nonisotopic Immunoassay,* Plenum Press, N.Y.

Further, the antibodies, including antigen binding fragments, of this invention can be potent antagonists that bind to the SPS and inhibit synthetase activity or the ability of the enzyme to function in another activity. They also can be useful as non-neutralizing antibodies and can be coupled to toxins or radionuclides so that when the antibody binds to SPS, a cell expressing it is killed. Further, these antibodies can be conjugated to drugs or other therapeutic agents, either directly or indirectly by means of a linker, and may effect drug targeting.

SPS fragments may be joined to other materials, particularly polypeptides, as fused or covalently joined polypeptides to be used as immunogens. An SPS and its fragments may be fused or covalently linked to a variety of immunogens, such as keyhole limpet hemocyanin, bovine serum albumin, tetanus toxoid, etc. See *Microbiology,* Hoeber Medical Division, Harper and Row, 1969; Landsteiner (1962) *Specificity of Serological Reactions,* Dover Publications, New York; Williams, et al. (1967) *Methods in Immunology and Immunochemistry,* vol. 1, Academic Press, New York; and Harlow and Lane (1988) *Antibodies: A Laboratory Manual,* CSH Press, NY, for descriptions of methods of preparing polyclonal antisera.

In some instances, it is desirable to prepare monoclonal antibodies from various mammalian hosts, such as mice, rodents, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.), Academic Press, New York; and particularly in Kohler and Milstein (1975) in *Nature* 256:495–497, which discusses one method of generating monoclonal antibodies.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277, 437; 4,275,149; and 4,366,241. Also, recombinant immunoglobulins may be produced, see Cabilly, U.S. Pat. No. 4,816,567; Moore, et al., U.S. Pat. No. 4,642,334; and Queen, et al. (1989) *Proc. Nat'l Acad. Sci. USA* 86:10029–10033.

The antibodies of this invention can also be used for affinity chromatography in isolating the protein. Columns can be prepared where the antibodies are linked to a solid support. See, e.g., Wilchek et al. (1984) *Meth. Enzymol.* 104:3–55.

Antibodies raised against each SPS will also be useful to raise anti-idiotypic antibodies. These will be useful in detecting or diagnosing various immunological conditions related to expression of the respective antigens.

Nucleic Acids

The described peptide sequences and the related reagents are useful in isolating a DNA clone encoding SPS, e.g., from a natural source. Typically, it will be useful in isolating a gene or cDNA from mouse or human, and similar procedures will be applied to isolate genes from other species, e.g., warm blooded animals, such as birds and mammals. See SEQ ID NO: 1 and 3. Cross hybridization will allow isolation of SPS from other species. A number of different approaches should be available to successfully isolate a suitable nucleic acid clone.

The purified protein or defined peptides are useful for generating antibodies by standard methods, as described above. Synthetic peptides or purified protein can be presented to an immune system to generate monoclonal or polyclonal antibodies. See, e.g., Coligan (1991) *Current Protocols in Immunology* Wiley/Greene; and Harlow and Lane (1989) *Antibodies: A Laboratory Manual,* Cold Spring Harbor Press.

For example, the specific binding composition could be used for screening of an expression library made from a cell line which expresses an SPS. Screening of intracellular expression can be performed by various staining or immunofluorescence procedures. The binding compositions could be used to affinity purify or sort out cells expressing SPS.

The peptide segments can also be used to predict appropriate oligonucleotides to screen a library. The genetic code can be used to select appropriate oligonucleotides useful as probes for screening. See, e.g., SEQ ID NO: 1 or 3. In combination with polymerase chain reaction (PCR) techniques, synthetic oligonucleotides will be useful in selecting correct clones from a library. Complementary sequences will also be used as probes or primers. Based upon identification of the likely amino terminus, the third peptide should be particularly useful, e.g., coupled with anchored vector or poly-A complementary PCR techniques or with complementary DNA of other peptides.

This invention contemplates use of isolated DNA or fragments to encode a biologically active corresponding SPS polypeptide. In addition, this invention covers isolated or recombinant DNA which encodes a biologically active protein or polypeptide which is capable of hybridizing under appropriate conditions with the DNA sequences described herein. Said biologically active protein or polypeptide can be intact, or a fragment, and have an amino acid sequence as disclosed in SEQ ID NO: 2 or 4. Further, this invention covers the use of isolated or recombinant DNA, or fragments thereof, which encode proteins which are homologous to an SPS or which are isolated using CDNA encoding an SPS as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule. Generally, the nucleic acid will be in a vector or fragment less than about 50 kb, usually less than about 30 kb, typically less than about 10 kb, and preferably less than about 6 kb.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid can be defined either by its method of production or its structure. In reference to its method of production, e.g., a product made by a process, the process is use of recombinant nucleic acid techniques, e.g., involving human intervention in the nucleotide sequence, typically selection or production. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site.

Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode polypeptides similar to fragments of these antigens, and fusions of sequences from various different species variants.

A significant "fragment" in a nucleic acid context is a contiguous segment of at least about 17 nucleotides, generally at least about 22 nucleotides, ordinarily at least about 29 nucleotides, more often at least about 35 nucleotides, typically at least about 41 nucleotides, usually at least about 47 nucleotides, preferably at least about 55 nucleotides, and in particularly preferred embodiments will be at least about 60 or more nucleotides.

A DNA which codes for an SPS protein will be particularly useful to identify genes, mRNA, and cDNA species which code for related or homologous proteins, as well as DNAs which code for homologous proteins from different species. There are likely homologues in other species, including primates. Various SPS proteins should be homologous and are encompassed herein. However, even proteins that have a more distant evolutionary relationship to SPS can readily be isolated under appropriate conditions using these sequences if they are sufficiently homologous. Primate SPS proteins are of particular interest.

Recombinant clones derived from the genomic sequences, e.g., containing introns, will be useful for transgenic studies, including, e.g., transgenic cells and organisms, and for gene therapy. See, e.g., Goodnow (1992) "Transgenic Animals" in Roitt (ed.) *Encyclopedia of Immunology,* Academic Press, San Diego, pp. 1502–1504; Travis (1992) *Science* 256:1392–1394; Kuhn, et al. (1991) *Science* 254:707–710; Capecchi (1989) *Science* 244:1288; Robertson (1987)(ed.) *Teratocarcinomas and Embryonic Stem Cells: A Practical Approach,* IRL Press, Oxford; and Rosenberg (1992) *J. Clinical Oncology* 10:180–199.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least about 58%, ordinarily at least about 65%, often at least about 71%, typically at least about 77%, usually at least about 85%, preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence of SEQ ID NO: 1 or 3. Typically, selective hybridization will occur when there is at least about 55% homology over a stretch of at least about 30 nucleotides, preferably at least about 75% over a stretch of about 25 nucleotides, and most preferably at least about 90% over about 20 nucleotides. See, Kanehisa (1984) *Nuc. Acids Res.* 12:203–213. The length of homology comparison, as described, may be over longer stretches, and in certain embodiments will be over a stretch of at least about 17 nucleotides, usually at least about 28 nucleotides, typically at least about 40 nucleotides, and preferably at least about 75 to 100 or more nucleotides.

Stringent conditions, in referring to homology in the hybridization context, will be stringent combined conditions of salt, temperature, organic solvents, and other parameters, typically those controlled in hybridization reactions. Stringent temperature conditions will usually include temperatures in excess of about 30° C., usually in excess of about 37° C., typically in excess of about 55° C., preferably in excess of about 70° C. Stringent salt conditions will ordinarily be less than about 1000 mM, usually less than about 400 mM, typically less than about 250 mM, preferably less than about 150 mM. However, the combination of parameters is much more important than the measure of any single parameter. See, e.g., Wetmur and Davidson (1968) *J. Mol. Biol.* 31:349–370.

SPS from other mammalian species can be cloned and isolated by cross-species hybridization of closely related species. See, e.g., below. Homology may be relatively low between distantly related species, and thus hybridization of relatively closely related species is advisable. Alternatively, preparation of an antibody preparation which exhibits less species specificity may be useful in expression cloning approaches.

Making SPS; Mimetics

DNA which encodes the SPS or fragments thereof can be obtained by chemical synthesis, screening cDNA libraries, or screening genomic libraries prepared from a wide variety of cell lines or tissue samples. See, e.g., Okayama and Berg (1982) *Mol. Cell. Biol.* 2:161–170; Gubler and Hoffman (1983) *Gene* 25:263–269; and Glover (ed.) (1984) *DNA Cloning: A Practical Approach,* IRL Press, Oxford.

This DNA can be expressed in a wide variety of host cells for the synthesis of a full-length protein or fragments which can in turn, e.g., be used to generate polyclonal or monoclonal antibodies; for binding studies; for construction and expression of modified molecules; and for structure/function studies.

Vectors, as used herein, comprise plasmids, viruses, bacteriophage, integratable DNA fragments, and other vehicles which enable the integration of DNA fragments into the genome of the host. See, e.g., Pouwels, et al. (1985 and Supplements) *Cloning Vectors: A Laboratory Manual,* Elsevier, N.Y.; Rodriguez, et al. (1988)(eds.) *Vectors: A Survey of Molecular Cloning Vectors and Their Uses,* Buttersworth, Boston, Mass.;

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression. See e.g., Rodriguez, et al., Chapter 10, pp. 205–236; Balbas and Bolivar (1990) *Methods in Enzymology* 185:14–37; and Ausubel, et al. (1993) *Current Protocols in Molecular Biology,* Greene and Wiley, NY.

Representative examples of suitable expression vectors include pCDNA1; pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610. See, e.g., Miller (1988) *Ann. Rev. Microbiol.* 42:177–199.

It will often be desired to express an SPS polypeptide in a system which provides a specific or defined glycosylation pattern. See, e.g., Luckow and Summers (1988) *Bio/Technology* 6:47–55; and Kaufman (1990) *Meth. Enzymol.* 185:487–511.

The SPS protein, or a fragment thereof, may be engineered to be phosphatidyl inositol (PI) linked to a cell membrane, but can be removed from membranes by treatment with a phosphatidyl inositol cleaving enzyme, e.g., phosphatidyl inositol phospholipase-C. This releases the antigen in a biologically active form, and allows purification by standard procedures of protein chemistry. See, e.g., Low (1989) *Biochim. Biophys. Acta* 988:427–454; Tse, et al. (1985) *Science* 230:1003–1008; and Brunner, et al. (1991) *J. Cell Biol.* 114:1275–1283.

Now that the SPS has been characterized, fragments or derivatives thereof can be prepared by conventional processes for synthesizing peptides. These include processes such as are described in Stewart and Young (1984) *Solid Phase Peptide Synthesis,* Pierce Chemical Co., Rockford, Ill.; Bodanszky and Bodanszky (1984) *The Practice of Peptide Synthesis,* Springer-Verlag, New York; and Bodanszky (1984) *The Principles of Peptide Synthesis,* Springer-Verlag, New York; and Villafranca (ed.) (1991) *Technioues in Protein Chemistry II,* Academic Press, San Diego, Calif.

Uses

The present invention provides reagents which will find use in diagnostic applications as described elsewhere herein, e.g., in the general description for developmental abnormalities, or below in the description of kits for diagnosis. These reagents will also find use in producing methods for incorporateing seleoncystein into selenoproteins, and as regulatory methods to control expression, e.g., of genes used in vectors for gene therapy. Highly controlled means to prevent expression which incorporate both transcriptional regulation and translatinal regulation may be very important in gene therapy applications. Combining a termination codon into a protein message as occurs in selenoproteins with tightly controlled transcriptional regulation can minimize danger of undesired expression of genes in gene therapy applications.

This invention also provides reagents with significant therapeutic value. The SPS protein (naturally occurring or recombinant), fragments thereof, and antibodies thereto, along with compounds identified as having binding affinity to SPS, should be useful in the treatment of conditions associated with abnormal physiology or development, including selenium poisoning. Moreover, the SPS may have an important role in detoxification of reactive iron compounds found, e.g., in hematopoietic cells which must fix iron into oxygen carrying heme. In addition, the SPS may be important in regulating damage by high oxygen environments of a cell, e.g., in the red blood cells. For example, a disease or disorder associated with abnormal iron or oxygen tolerance may be susceptible to control by SPS or selenoproteins which would be regulated by SPS or contain selenocysteine. The protein likely plays a role in regulation or development of hematopoietic cells, e.g., lymphoid cells, which affect immunological responses, e.g., autoimmune disorders.

Other abnormal developmental conditions are known in each of the cell types shown to possess SPS mRNA by Northern blot analysis. See Berkow (ed.) *The Merck Manual of Diagnosis and Therapy,* Merck & Co., Rahway, N.J.; and Thorn, et al. *Harrison's Principles of Internal Medicine,* McGraw-Hill, N.Y.

Recombinant SPS or SPS antibodies can be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using SPS or fragments thereof can be performed to identify compounds having binding affinity to or modulatory effects on SPS, including isolation of associated components. For instance, it would be desireable to screen for modulators of the enzyme which, e.g., modulate the enzyme activity by at least about 10%, preferably at least 20%, and more preferably at least 30% or more. Subsequent biological assays can then be utilized to determine if the compound has intrinsic stimulating activity. Likewise, a compound having intrinsic blocking activity can deactivate the enzyme, and may serve as a competitive inhibitor, or may kill the activity. This invention further contemplates the therapeutic use of antibodies to SPS. This approach should be particularly useful with other SPS protein species variants.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 1 fM (femtomolar), with an appropriate carrier. Slow release formulations, or a slow release apparatus will often be utilized for continuous administration. See, e.g., Langer (1990) *Science* 249:1527–1533.

SPS, fragments thereof, and antibodies to it or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient, usually a sterile composition is desired. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; Avis, et al. (eds.) (1993) *Pharmaceutical Dosage Forms: Parenteral Medications,* Dekker, New York; Lieberman, et al. (eds.) (1990) *Pharmaceutical Dosage Forms: Tablets,* Dekker, New York; and Lieberman, et al. (eds.) (1990) *Pharmaceutical Dosage Forms: Disperse Systems,* Dekker, New York. The therapy of this invention may be combined with or used in association with other agents.

Both the naturally occurring and the recombinant forms of the SPS proteins of this invention are particularly useful in kits and assay methods which are capable of screening compounds for binding activity to the proteins. Several methods of automating assays have been developed in recent years so as to permit screening of tens of thousands of compounds in a short period. See, e.g., Fodor, et al. (1991) *Science* 251:767–773, which describes means for testing of binding affinity by a plurality of defined polymers synthesized on a solid substrate. The development of suitable assays can be greatly facilitated by the availability of large amounts of purified, soluble SPS protein as provided by this invention.

For example, antagonists can normally be found once the protein has been structurally defined. Testing of potential analogs is now possible upon the development of highly automated assay methods using a purified SPS target protein. In particular, new agonists and antagonists will be discovered by using screening techniques described herein. Of particular importance are compounds found to have ability to modulate the enzyme activity. These compounds may well have ability to modulate the intracellular acitivity of the protein, and thus affect the regulation of selenoproteins, particularly those containing selenocysteine. As indicated above, the tissue distribution suggests that this enzyme is distributed in tissues where a role in oxidation or metal toxicity may be regulated.

Another technique for drug screening involves an approach which provides high throughput screening for compounds having suitable binding affinity to an SPS target protein and is described in detail in Geysen, European Patent Application 84/03564, published on Sep. 13, 1984. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified SPS protein, or antibodies to SPS, and washed. The next step involves detecting bound SPS protein or the antibodies. This allows determination of what structures will interact with the tested compounds.

Rational drug design may also be based upon structural studies of the molecular shapes of the SPS protein and other effectors or analogues. Effectors may be other proteins which mediate other functions in response to synthetase activity. One means for determining which sites interact with specific other proteins is a physical structure determination, e.g., x-ray crystallography or 2 dimensional NMR techniques. These will provide guidance as to which amino acid residues form molecular contact regions. For a detailed description of protein structural determination, see, e.g., Blundell and Johnson (1976) *Protein Crystallography,* Academic Press, New York.

Kits

This invention also contemplates use of SPS proteins, fragments thereof, peptides, and their fusion products, and nucleic acids in a variety of diagnostic kits and methods for detecting the presence of SPS protein, antibodies, or genes and messages. Typically the kit will have a compartment containing either a defined SPS peptide or gene segment or a reagent which recognizes one or the other, e.g., antibodies.

A kit for determining the binding affinity of a test compound to an SPS protein would typically comprise a test compound; a labeled compound, for example an antibody having known binding affinity for the protein; a source of SPS protein (naturally occurring or recombinant); and a means for separating bound from free labeled compound, such as a solid phase for immobilizing the protein. Once compounds are screened, those having suitable binding affinity to the protein can be evaluated in suitable biological assays, as are well known in the art, to determine whether they act as agonists or antagonists to the synthetase activity. The availability of recombinant SPS polypeptides also provide well defined standards for calibrating such assays, or even as standards for enzymatic assays, e.g., production of selenophosphate. The SPS can also be labeled easily with radioactive selenium.

A preferred kit for determining the concentration of, for example, an SPS protein in a sample would typically comprise a labeled compound, e.g., an antibody, having known binding affinity for the protein, a source of protein (naturally occurring or recombinant) and a means for separating the bound from free labeled compound, for example, a solid phase for immobilizing the SPS protein. Compartments containing reagents, and instructions, will normally be provided.

Antibodies, including antigen binding fragments, specific for the SPS protein or polypeptide fragments are useful in diagnostic applications to detect the presence of elevated levels of SPS protein and/or its fragments. Such diagnostic assays can employ lysates, live cells, fixed cells, immunofluorescence, cell cultures, body fluids, and further can involve the detection of antigens related to the protein in serum, or the like. Diagnostic assays may be homogeneous (without a separation step between free reagent and antigen-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA), and the like. See, e.g., Van Vunakis, et al. (1980) *Meth Enzymol.* 70:1–525; Harlow and Lane (1980) *Antibodies: A Laboratory Manual,* CSH Press, NY; and Coligan, et al. (eds.) (1993) *Current Protocols in Immunology,* Greene and Wiley, NY.

Anti-idiotypic antibodies may have similar use to diagnose presence of antibodies against an SPS protein, as such may be diagnostic of various abnormal states. For example, overproduction of SPS protein may result in production of various immunological reactions which may be diagnostic of abnormal physiological states, particularly in proliferative cell conditions such as cancer or abnormal differentiation.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled SPS protein is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium providing appropriate concentrations of reagents for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the protein, test compound, SPS protein, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Possibilities for indirect labeling include biotinylation of one constituent followed by binding to avidin coupled to one of the above label groups.

There are also numerous methods of separating the bound from the free protein, or alternatively the bound from the free test compound. The SPS protein can be immobilized on various matrixes followed by washing. Suitable matrixes include plastic such as an ELISA plate, filters, and beads. See, e.g., Coligan, et al. (eds.) (1993) *Current Protocols in Immunology*, Vol. 1, Chapter 2, Greene and Wiley, NY. Other suitable separation techniques include, without limitation, the fluorescein antibody magnetizable particle method described in Rattle, et al. (1984) *Clin. Chem.* 30:1457–1461, and the double antibody magnetic particle separation as described in U.S. Pat. No. 4,659,678.

Methods for linking proteins or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of an SPS protein. These sequences can be used as probes for detecting levels of the protein message in samples from patients suspected of having an abnormal condition, e.g., cancer or developmental problem. The preparation of both RNA and DNA nucleotide sequences, the labeling of the sequences, and the preferred size of the sequences has received ample description and discussion in the literature. See, e.g., Langer-Safer, et al. (1982) *Proc. Nat'l. Acad. Sci.* 79:4381–4385; Caskey (1987) *Science* 236:962–967; and Wilchek et al. (1988) *Anal. Biochem.* 171:1–32.

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

The broad scope of this invention is best understood with reference to the following examples, which are not intended to limit the invention to specific embodiments.

EXAMPLES

General Methods

Some of the standard methods are described or referenced, e.g., in Maniatis, et al. (1982) *Molecular Cloning, A Laboratory Manual*, Cold Spring Harbor Laboratory, Cold Spring Harbor Press; Sambrook, et al. (1989) *Molecular Cloning: A Laboratory Manual* (2d ed.), vols 1–3, CSH Press, NY; Ausubel, et al., *Biology*, Greene Publishing Associates, Brooklyn, NY; or Ausubel, et al. (1987 and Supplements) *Current Protocols in Molecular Biology*, Greene and Wiley, New York; Innis, et al. (eds.) (1990) *PCR Protocols: A Guide to Methods and Applications*, Academic Press, N.Y. Methods for protein purification include such methods as ammonium sulfate precipitation, column chromatography, electrophoresis, centrifugation, crystallization, and others. See, e.g., Ausubel, et al. (1987 and periodic supplements); Deutscher (1990) "Guide to Protein Purification" in *Methods in Enzymology* vol. 182, and other volumes in this series; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See, e.g., Hochuli (1989) *Chemische Industrie* 12:69–70; Hochuli (1990) "Purification of Recombinant Proteins with Metal Chelate Absorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc., Chatsworth, Calif. Cell culture techniques are described in Doyle, et al. (eds.) (1994) *Cell and Tissue Culture: Laboratory Procedures*, John Wiley and Sons, NY.

FACS analyses are described in Melamed, et al. (1990) *Flow Cytometry and Sorting* Wiley-Liss, Inc., New York, N.Y.; Shapiro (1988) *Practical Flow Cytometry* Liss, New York, N.Y.; and Robinson, et al. (1993) *Handbook of Flow Cytometry Methods* Wiley-Liss, New York, N.Y.

Animals

Timed pregnant ICR female mice (Harlan Sprague Dawley, Indianapolis, Ind.) had the vaginal plugs checked after breeding, the morning of the day when the vaginal plug was found was designated as day 0. Somite pairs were carefully counted and 3 to 6 somite stage embryos were designated as 8.0 day embryos. The mice were sacrificed by $CO_2$ narcosis and dissected under a dissecting microscope. Tissue samples were collected in phosphate buffered saline (PBS)+5% (vol/vol) fetal calf serum and kept on ice during dissection, centrifuged at 1,000 rpm for 5 minutes, supernatants were aspirated and pellets were frozen in dry ice before storage at −80°C.

Three week old Balb/c male mice were sacrificed, as above, for the extraction of multiple organs. A sample of peri-visceral abdominal fat was extracted from the splenic region. Bone marrow cells were extracted from femurs and tibias by flushing their interior with PBS+5% fetal calf serum, filtered through a 70 mm nylon Cell Strainer (Becton Dickinson, Franklin Lakes, N.J.), centrifuged, and pellets were processed as above.

Cell Culture

ES cells were used as previously described by McClanahan, et al. (1993) *Blood* 81:2903–2915. Briefly, ES cells (cell line CCE) were maintained on gelatin-coated tissue culture dishes in Dulbecco's Modified Eagle Media+ 20% fetal calf serum (Gemini Bioproducts, Calabasas, Calif.) supplemented with 4 mM L-Glutamine (JRH Biosciences, Lenexa, Kans.), 100 U/ml penicillin, 100 $\mu$g/ml streptomycin, 0.1 mM nonessential amino-acids (GIBCO, Grand Island, N.Y.), 0.1 mM 2-mercaptoethanol (Sigma, St Louis, Mo.) plus 2,500 U/ml recombinant Leukemia Inhibitory Factor (rLIF). Embryoid bodies were maintained in ES medium without rLIF and generated by plating $1.0 \times 10^5$ ES. cells/ml in 10 cm bacterial Petri dishes (Baxter, McGraw Park, Ill.). The cultures were fed every 3 days and kept at 37° C. in a humidified 5% $CO_2$ atmosphere.

STO cells were maintained in Dulbecco's Modified Eagle's Media+5% fetal calf serum. N2a cells were kept in Dulbecco's Modified Eagle's Media+10% Horse Serum (GIBCO BRL) containing 100 U/ml penicillin and 100 $\mu$g/ml streptomycin. FDCPmixA4 cells were maintained in Iscove Modified Eagle Media+20% horse serum containing 50 $\mu$M 2-mercaptoethanol, 100 U/ml penicillin, 100 mg streptomycin and 100 U/ml mouse IL-3 (DNAX Research Institute, Palo Alto, Calif.).

Cell lines were plated in tissue culture dishes at a concentration of 1×10⁵ cells/ml and kept at 37° C. in a humidified atmosphere with 5% $CO_2$. STO and N2a cells were collected before confluence, treated with 0.25% trypsin and 1 mM EDTA in PBS, centrifuged as above, and pellets were frozen before storage at −80° C. The same protocol was used for the FDCPmixA4 cells but without trypsinization.

T Lymphocyte Sorting and Stimulation

Eight week-old female BALB/c mice were purchased from Jackson Laboratories (Bar Harbor, Me.). Single cell suspensions were made from peripheral lymph nodes, depleted of B lymphocytes using sheep anti-mouse IgG coated magnetic beads (Dynal, Oslo, Norway), and labeled with appropriate dilutions of anti-CD4-phycoeryhtrin and anti-CD8-fluorescein isothiocyanate antibodies (Pharmingen, San Diego, Calif.). $CD4^+8-$ and $CD4-8+$ T lymphocytes were sorted by flow cytometry using a FACS vantage cell sorter (Becton Dickinson, San Jose, Calif.). Purity upon reanalysis was 99.8%. Sorted subpopulations were resuspended in RPMI 1640 medium (JRH Biosciences, Lenexa, Kans.) supplemented with 10% FCS, 200 mM L-glutamine, 5×10⁻⁵ M mercaptoethanol, MEM amino acids and vitamins, sodium bicarbonate, penicillin, streptomycin (all from SIGMA), and then plated at 10⁶ cells/ml in 24-well plates (Becton Dickinson, Lincoln Park, N.J.) coated with 10 µg/ml anti-CD3 (Pharmingen). Cells were harvested after 16 h of anti-CD3 stimulation and frozen before RNA extraction. CD4+8− T helper cells can be divided in Th1 and Th2 subsets based on their cytokine production and functions. Th1 polarized CD4+8− T cells were recovered from lymph nodes of BALB/c mice infected with Leishmania major and treated with anti-CD4 antibody. Th2 polarized CD4+8− T cells were recovered from lymph nodes of BALB/c mice infected with Leishmania major without anti-CD4 antibody treatment. In both cases, CD4+8− were purified from lymph nodes by Magnetic Activated Cell Sorting and purity was greater than 98%.

RNA Extraction

RNA was isolated from 5 to 10×10⁷ cells, a pellet of equivalent size, whenever available, from embryonic tissues, or from a complete adult organ using RNAzol solution (Tel-test, Inc, Friendswood, Tex.) following manufacturer's instructions. Heart and testis total RNAs were purchased from Clontech, Palo Alto, Calif.

Differential Display by PCR (DD-PCR)

Reverse transcription and PCR conditions were as suggested by GenHunter Corporation (Brookline, Mass.). All reagents were from the RNAmap kit (Genhunter), except AmpliTaq DNA polymerase (Perkin Elmer-Cetus, Norwalk, Conn.) and ³⁵S-dATP (Amersham, Arlington Heights, Ill.). A duplicate reverse transcription reaction was performed for each sample and a PCR reaction was done for each of the duplicate cDNAs and run side by side in the same polyacrylamide gel in order to evaluate the reproducibility of the results.

A DNA ladder was prepared by labeling the 5' end of DNA Marker V (Boehringer Mannheim) for sizing purposes. The PCR products were run on denaturing 6% polyacrylamide gels. Gels were dried and exposed to Kodak O-mat film (Eastman Kodak, Rochester, N.Y.) for 2 to 5 days.

Cloning and Sequencing of the PCR Products

Specific bands were cut from the gels after long runs for better resolution of the bands. Film and gel were oriented and DNA was extracted from the dried gel and reamplified by PCR, following manufacturer's instructions (GenHunter Corporation). Reamplified PCR products were run in 3% NuSieve 3:1 Agarose gels (FMC Bioproducts, Rockland, Me.), gel extracted using the QIAEX extraction kit (QIAGEN Inc, Chatsworth, Calif.), cloned using the TA Cloning kit (Invitrogen, San Diego, Calif.), and mini preps DNA were obtained using the RPM kit (BIO 101, Inc, Vista, Calif.) following manufacturer's instructions.

Three independent clones derived from each polyacrylamide gel slice were sequenced using the 70750 Reagent Kit For Sequencing With Sequenase T7 DNA Polymerase and 7-deaza-dGTP (Amersham, Cleveland, Ohio) in order to exclude the possibility of more than one PCR product being represented as a single band in the polyacrylamide gel.

Northern Blot Analysis

Large preparations of plasmid DNA containing the PCR products were done using the QIAGEN Plasmid Maxi Kit (QIAGEN) following the manufacturer's instructions. Plasmid DNA was cut with Eco RI (Boeheringer Mannheim) or Bst XI (Biolabs, New England), gel extracted with the QIAEX gel extraction kit (QIAGEN), and random primed with ³²P-dCTP (Amersham) using the Prime-It II kit (Stratagene, La Jolla, Calif.), all in accordance with manufacturer's instructions. The 3' primer (0.03 pM final concentration) used to generate the PCR product was included in the labeling reaction as suggested (GenHunter Corporation).

10 to 20 µg of total RNA were run, after heating the samples at 55° C. for 15 min, in formaldehyde gels (per 100 ml gel solution: 1.2% agarose [FMC Bioproducts], 10 ml 10×MOPS-EDTA-Sodium Acetate Buffer [Sigma, St Louis, Mo.], 5,5 ml formaldehyde [Sigma]; per 20 µl sample to be loaded: 4,5 µl RNA sample, 10 µl formamide [Sigma], 3.5 µl formaldehyde [Sigma] and 2 µl 10×MOPS) and transferred to Nytran membranes (Schleider & Schuell, Keene, N.H.) by standard methods. Blots were hybridized at 65° C. in 0.5 M $NaHPO_4$ pH 7.2, 7% SDS and 0.5 M EDTA, pH 8.0 for 24 hours, then washed at 65° C. in 2×SSC, 0.1% SDS for 30 min with one change of buffer, followed by a wash at 65° C. in 0.2×SSC, 0.1% SDS for 30 min, also with a change of buffer, and exposed to film at −80° C.

cDNA Cloning and Sequence Analysis

PolyA⁺ RNA was obtained from total FDCPmixA4 RNA using the Oligotex-dT mRNA kit (QIAGEN) following the manufacturer's instructions and 5 µg were used to make a cDNA library. The Superscript Plasmid System (GIBCO BRL) was used for the cDNA synthesis, λ Not I—Sal I Arms (GIBCO BRL) were ligated to the cDNA and packaged using the λ Packaging System (GIBCO BRL). Phage were plated at a density of 30,000 plaque forming units per plate and screened using the probe derived from the cloned PCR products, as above. Filters (Hybond-N⁺, Amersham) were hybridized at 65° C. as described for the Northern Analysis. Phage were subcloned into pZL1 plasmids (GIBCO) using DH10B cells (GIBCO) and λ Ziplox Not I—Sal I Arms (GIBCO).

A full length human SPS cDNA was isolated from a cDNA library derived from activated CD8⁺ T cells, see Cocks et al. (1993) *International Immunology* 5:657–663, by standard methods (Sambrook, et al. (1989)) using a cDNA complementary to SPS as a probe. The SPS specific cDNA was generated by PCR using CD8+ T cell cDNA as a template and the primers: sense primer: 5' GTAAAGATG-GTGGTCTCCAG 3' and antisense: 5' CTCTCCCGTACT-TGGAGGATTTG 3'. These primers were designed from the sequence of the EST T09327, a 426 base pairs sequence found to represent a human homologue of mouse and bacterial SPS.

Constructs

The mouse SPS translating region was amplified by PCR in order to introduce a FLAG peptide sequence (IBI, New Haven, Conn.) between the first and second aminoacids of SPS—sense primer: 5' ACTTCTCGAGGCACCATGGAC-TACAAGGACGACGATGACAAGGCG-GAAGCGGCGGCGGCGGGC 3'; antisense primer: 5' CTAGGTCTAGATTCAAGAACTAG-GCTCAGAGGCTGC 3'. PFU enzyme (Stratagene) was used with 12 cycles PCR: 94° C. 30 seconds; 55° C. for 1 min; 72° C. for 4 min. This SPS construct was cloned into the PME18X vector using the XhoI and XbaI sites that had been also incorporated into the 5' and 3' primers, respectively. The codon 63 (UGA) was mutated to UGC by PCR mutagenesis in the CYS (cysteine) mutant.

Transfections

COS-7 cells were maintained in DMEM, 10% fetal calf serum, 4 mM L-Glutamine (JRH Biosciences, Lenexa, Kans.), 100 U/ml penicillin and 100 μg/ml streptomycin. Plasmid DNA was transfected by electroporation (BIORAD, Hercules, Calif.) (20 μg/1×10$^7$ cells) and plated into tissue culture dishes. The media was replaced after 24 hours and cell lysates were collected three days after transfection.

Immunoprecipitations

Lysis buffer (25 mM Hepes, pH 7.5, 2 mM EDTA, 1.0% NP-40, 150 mM NaCl, 0.1% SDS, 0.01% Aprotinin (Sigma), 0.01% Leupeptin (Sigma)) was added to the plates. Plates were kept on ice for 45 min. Lysates were centrifuged for 15 minutes to eliminate cell debris. Supernatants were incubated with anti-Flag M2 Affinity Gel (IBI) at 4° C. overnight and washed three to four times with PBS before elution at 95° C. for 5 minutes in 2×Sample Buffer (Novex, San Diego, Calif.). Cells grown for 4 days in media containing 5% fetal calf serum were used in the experiments with $^{75}$Se (University of Missouri Research Reactor Facility, Columbia, Mo.) and transfected cells grew in media with 10% serum+0.1 mCi $^{75}$Se/L. Immunoprecipitates were eluted in a Econocolumn (BIORAD) with 2.5 M Glycine, pH 2.5. Eluates were neutralized with Hepes, pH 7.4 (JRH Biosciences) and concentrated by precipitation with 24% TCA and 2% deoxycholic sodium salt (Sigma).

Western Blotting

Immunoprecipitated proteins were electrophoresed on 4–20% tris-glycine gels (Novex) and transferred to PVDF membranes (Immobilon-P, Millipore Corporation, Bedford, Mass.). Membranes were exposed to 3% non-fat milk for 1 h at 37° C. Anti-Flag M2 and Anti-Flag M1 antibodies were used as recommended (IBI). Anti-mouse Ig horseradish peroxidase conjugate (Amersham) was used at 1:2,000 dilution and the peroxidase detection was performed with ECL detection reagents (Amersham). Western Blots from $^{75}$Se labeled immmunoprecipitates were exposed to Phosphor screen (Molecular Dynamics, Sunnyvale, Calif.).

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An isolated or recombinant polynucleotide encoding sequence comprising a mature polypeptide of SEQ ID NO: 4, or an enzymatically active fragment thereof.

2. The polynucleotide of claim 1, wherein said polynucleotide:
   a) is from a natural source;
   b) is from a mammal;
   c) comprises a natural full length coding sequence;
   d) forms a nucleic acid duplex with a complementary polynucleotide;
   e) is double stranded; or
   f) comprises a ribonucleotide.

3. A polynucleotide which hybridizes under stringent wash conditions of at least 50° C. and less than about 150 mM salt to a complement of SEQ ID NO: 3 wherein said polynucleotide encodes a polypeptide having enzymatic activity.

4. The polynucleotide of claim 1, wherein said fragment is at least 30 contiguous residues.

5. The polynucleotide of claim 4, further encoding at least 12 contiguous residues.

6. An isolated or recombinant polynucleotide encoding sequence comprising a mature polypeptide of SEQ ID NO: 2, or an enzymatically active fragment thereof.

7. The isolated polynucleotide of claim 6, comprising nucleotides 138–1493 of SEQ ID NO: 1.

8. The recombinant polynucleotide of claim 1, wherein said polynucleotide is operably linked in an expression vector, and
   a) said expression vector further comprises a promoter;
   b) said expression vector further comprises an origin of replication; or
   c) said polynucleotide comprises an internal in frame termination codon that encodes a selenocysteine.

9. The polynucleotide of claim 1, wherein said polynucleotide:
   a) is detectably labeled;
   b) comprises synthetic nucleotide sequence; or
   c) is less than 6 kb.

10. An isolated polynucleotide which hybridizes under stringent conditions of at least 50° C. and less than about 150 mm salt to a complement of SEQ ID NO: 1, wherein said polynucleotide encodes a polypeptide having enzymatic activity.

11. A method of:
   a) making a polypeptide, comprising expressing said polynucleotide of claim 1, thereby producing said polypeptide; or
   b) immunizing an animal, comprising introducing said polynucleotide of claim 1 into said animal, thereby producing an antibody.

12. The polynucleotide of claim 1, wherein said polynucleotide is:
   a) antigenic; or
   b) fused to a purification tag.

13. A method of making a polynucleotide, comprising amplifying said polynucleotide of claim 3 using a polymerase chain reaction.

14. A method of producing a polypeptide, comprising culturing said cell of claim 4 under conditions resulting in the production of said polypeptide.

15. A method of:
   a) making polypeptide, comprising expressing said polynucleotide of claim 6, thereby producing said polypeptide; or
   b) immunizing an animal, comprising introducing said polynucleotide of claim 6 into said animal, thereby producing an antibody.

16. A method of transforming or transfecting a cell, comprising introducing a polynucleotide of claim 6 into said cell.

17. The polynucleotide of claim 6, wherein said sequence is:
   a) is detectably labeled;
   b) fused to a purification tag;

c) antigenic;

d) comprises synthetic nucleotide sequence; or e) is less than 6 kb.

18. A method of making a polynucleotide, comprising amplifying said polynucleotide of claim 10 using a polymerase chain reaction.

19. A cell transfected with said polynucleotide of claim 6.

20. A method of producing a polypeptide, comprising culturing said cell of claim 19 under conditions resulting in the production of said polypeptide.

21. An isolated or recombinant polynucleotide complementary to a polynucleotide of claim 1.

22. A cell comprising said polynucleotide of claim 6.

* * * * *